United States Patent [19]
Kawamoto et al.

[11] Patent Number: 4,771,046
[45] Date of Patent: Sep. 13, 1988

[54] CARBAPENEM DERIVATIVES

[75] Inventors: Isao Kawamoto; Rokuro Endo; Masayuki Iwata, all of Tokyo, Japan

[73] Assignee: Sankyo Company, Limited, Tokyo, Japan

[21] Appl. No.: 856,696

[22] Filed: Apr. 25, 1986

[30] Foreign Application Priority Data

Apr. 27, 1985 [JP] Japan .................................. 60-91988

[51] Int. Cl.$^4$ ................... C07D 487/04; A61K 31/40
[52] U.S. Cl. .................................... 514/210; 540/350
[58] Field of Search ......................... 540/350; 514/210

[56] References Cited

U.S. PATENT DOCUMENTS 4,477,662 10/1984 Corbett .............................. 540/350

FOREIGN PATENT DOCUMENTS 71908 2/1983 European Pat. Off. ............ 560/350
178888 9/1985 Japan .................................. 560/350

Primary Examiner—Robert Gerstl
Attorney, Agent, or Firm—Frishauf, Holtz, Goodman & Woodward

[57] ABSTRACT

Carbapenem derivatives useful as antibacterial agents have the formula

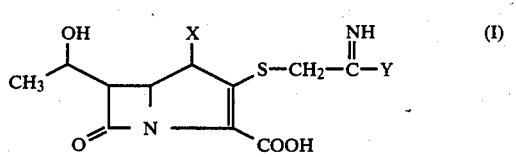

wherein:

X represents a hydrogen atom or a methyl group; and
Y represents a group of the formula:

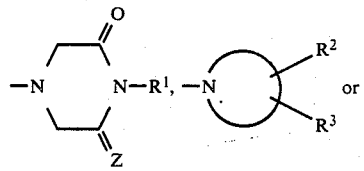

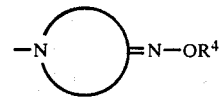

in which:

Z represents an oxygen atom or two hydrogen atoms;
$R^1$ represents a hydrogen atom, a $C_{1-4}$ alkyl group, a $C_{1-4}$ alkanoyl group, or a $C_{1-4}$ alkanesulfonyl group;
$R^2$ represents a hydrogen atom or a hydroxy group; and $R^3$ represents a carbamoyl group; or
$R^2$ represents a carbamoyloxy group, and $R^3$ represents a hydrogen atom or a carbamoyl group;
$R^4$ represents a hydrogen atom or a $C_{1-4}$ alkyl group; and

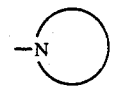

represents a 4–6 membered saturated heterocyclic group in which the indicated nitrogen atom is the only hetero-atom;
or a pharmaceutically acceptable salt or ester thereof.

19 Claims, No Drawings

CARBAPENEM DERIVATIVES

BACKGROUND TO THE INVENTION

The present invention relates to a series of new carbapenem compounds and to compositions containing the compounds, and provides processes for preparing these compounds.

The penicillins form a well known class of antibiotics, which have found considerable use in human and animal therapy for many years. Chemically, the penicillins have in common a β-lactam structure, commonly referred to as "penam", which may be represented by the following formula:

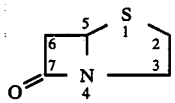

However, although the penicillins still form a valuable weapon in the pharmaceutical armory, the development of new, and often penicillin-resistant, strains of pathogenic bacteria has increasingly made it necessary to search for new types of antibiotic.

In recent years, great interest has been shown in compounds having a carbapenem structure, that is compounds having a carbon atom in place of the sulfur atom at the 1-position and having a double bond between the carbon atoms in the 2- and 3-positions of the basic penam structure. The carbapenem structure may be represented by the following formula:

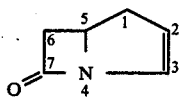

These penam and carbapenem structures form the basis for the semi-systematic nomenclature of the penicillin derivatives in accordance with the recommendations of the International Union of Pure and Applied Chemistry (IUPAC), and this nomenclature is generally accepted by those skilled in the art throughout the world and is used herein. The numbering system employed herein is that illustrated on the above formulae.

Of the known carbapenem derivatives, the best known is a compound called "thienamycin", whose semi-systematic name is 2-(2-aminoethylthio)-6-(1-hydroxyethyl)carbapen-2-em-3-carboxylic acid. Although thienamycin is known to have remarkably potent and broad antibacterial activity, its chemical stability in the human body is poor, which restricts its practical use. Various attempts have, therefore, been made to modify the chemical structure of thienamycin in order to improve its chemical stability whilst maintaining or improving its superior activity, but there is still a continuing need to develop further carbapenem antibiotics with improved properties.

Accordingly, it is an object of the present invention to provide a new group of carbapenem derivatives which possess superior absorption and metabolic stability (as evidenced by improved recovery rates in the urine), as well as a broad antibacterial spectrum and low toxicity. Further objects of the invention are to provide synthetic processes for the preparation of the said new carbapenem derivatives, and to provide pharmaceutical compositions comprising the said derivatives suitable for human and animal administration.

BRIEF SUMMARY OF THE INVENTION

In accordance with these objects, the invention provides compounds having the formula:

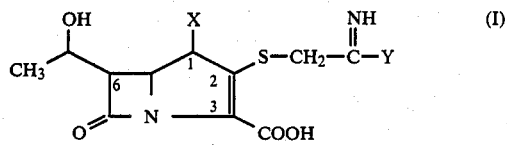

wherein:
X represents a hydrogen atom or a methyl group; and
Y represents a group of the formula:

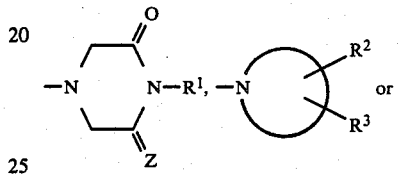

in which:
Z represents an oxygen atom or two hydrogen atoms;
$R^1$ represents a hydrogen atom, a $C_{1-4}$ alkyl group, a $C_{1-4}$ alkanoyl grpoup, or a $C_{1-4}$ alkanesulfonyl group;
$R^2$ represents a hydrogen atom or a hydroxy group, and $R^3$ represents a carbamoyl group;
$R^2$ represents a carbamoyloxy group, and $R^3$ represents a hydrogen atom or a carbamoyl group;
$R^4$ represents a hydrogen atom or a $C_{1-4}$ alkyl group; and

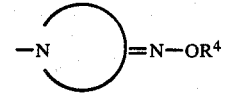

represents a 4–6 membered saturated heterocyclic group in which the indicated nitrogen atom is the only hetero-atom;
together with the pharmaceutically acceptable salts and esters thereof.

Of the prior art presently known to the applicants, that which comes closest to the present invention is believed to be in European Patent Publications Nos. 50334 and 71908. These diclose large groups of carbapenem compounds, with many possible alternatives for the substituents at positions 2 and 6 and (in the case of EP No. 71908) position 1 of the carbapenem nucleus. This prior art does not disclose any of the specific compounds of the present invention. Among the various combinations of substituents which are listed therein in tabular form, those which appear to come closest to the present invention are compounds corresponding to the above formula (I) wherein Y represents a 4-methylpiperazinyl, or an unsubstituted pyrrolidinyl or piperidinyl group; but there is no specific disclosure of the preparation of any of these individual compounds or of their properties.

DETAILED DESCRIPTION OF THE INVENTION

In the compounds of the invention, when $R^1$ represents a $C_{1-4}$ alkyl group this may be straight or branched, for example methyl, ethyl, propyl, isopropyl, butyl, isobutyl, sec-butyl or t-butyl. When $R^1$ represents a $C_{1-4}$ alkanoyl group this may be straight or branched, for example formyl, acetyl, propionyl, butyryl or isobutyryl. When $R^1$ represents a $C_{1-4}$ alkanesulfonyl group, the alkane portion of this may be, for example, any of the above-mentioned $C_{1-4}$ alkyl groups.

When $R^4$ represents a $C_{1-4}$ alkyl group it may be, for example, any of those mentioned above for $R^1$.

The 4-6 membered nitrogen-containing saturated heterocyclic group may be, for example, azetidinyl, pyrrolidinyl or piperidyl.

A preferred sub-group of the compounds of the invention are those wherein $R^1$ represents a hydrogen atom, a methyl group, an acetyl group or a mesyl (i.e. methanesulfonyl) group. Also preferred are those compounds in which Y represents a 3-oxopiperazin-1-yl, 4-methyl-3-oxopiperazin-1-yl, carbamoyloxypyrrolidin-1-yl, hydroxyiminopiperidin-1-yl or methoxyiminopiperidin-1-yl group. Particularly preferred compounds are those wherein $R^1$ represents a hydrogen atom or a methyl group, and Y represents a 3-oxopiperazin-1-yl or 4-methyl-3-oxopiperazin-1-yl group.

Although the compounds of the invention are represented in formula (I) in the form of neutral compounds, it will readily be appreciated by those skilled in the art that they can also exist in an amphoteric (or "zwitterionic" or "internal salt") form, in which the basic function of group Y is protonated and positively charged, and the carboxyl group at position 3 is deprotonated and negatively charged. The two forms will generally coexist in equilibrium with each other, and both are included within the scope of the invention.

The compounds of the invention, being acids, are also capable of forming external salts and esters. The nature of such salts and esters is not critical to the present invention and the compounds of formula (I) are capable of forming salts and esters with any cations and ester-forming alcohols, respectively, which are known for the formation of salts and esters with compounds of this type. The only restriction on the nature of such salts and esters is that they should be "pharmaceutically acceptable" which means to those skilled in the art that the salt-forming cation or ester-forming alcohol should not, or should not to an unacceptable extent, reduce the activity of the compounds of formula (I), nor should they increase, or increase to an unacceptable extent, the toxicity of those compounds. However, the formation of salts and esters and the application of these criteria to the choice of salt-forming cations or ester-forming alcohols is so well-known to the man skilled in the art as to require no further definition here.

Examples of suitable esters include: $C_1$-$C_6$ preferably $C_1$-$C_4$, alkyl esters, such as the methyl, ethyl, propyl, isopropyl, butyl, isobutyl and t-butyl esters; $C_1$-$C_6$, preferably $C_1$-$C_4$, haloalkyl esters, which may have one or more halogen atoms (the maximum number of halogen atoms being dictated by the number of carbon atoms in the alkyl group, but preferably being from 1 to 3), such as the 2-iodoethyl, 2,2-dibromoethyl and 2,2,2-trichloroethyl esters; alkoxymethyl esters, wherein the alkoxy part has from 1 to 6, preferably from 1 to 4, carbon atoms, for example the methoxymethyl, propoxymethyl, isopropoxymethyl, butoxymethyl and isobutoxymethyl esters; aliphatic carboxylic acyloxymethyl esters, wherein the acyl part which may have saturated or unsaturated carbon-carbon bonds, preferably all saturated, has from 2 to 7, preferably from 2 to 5, carbon atoms, for example the acetoxymethyl, propionyloxymethyl, butyryloxymethyl, isobutyryloxymethyl and pivaloyloxymethyl esters; 1-alkoxycarbonyloxyethyl esters, where the alkoxy part has from 1 to 6, preferably from 1 to 4, carbon atoms, for example the 1-methoxycarbonyloxyethyl, 1-ethoxycarbonyloxyethyl, 1-propoxycarbonyloxyethyl, 1-isopropoxycarbonyloxyethyl, 1-butoxycarbonyloxyethyl and 1-isobutoxycarbonyloxyethyl esters; aralkyl esters, where the aryl part has from 6 to 10 ring carbon atoms and is unsubstituted or has one or more (preferably from 1 to 3) substituents selected from the group consisting of those substituents listed above as possible substituents on ring carbon atoms (and preferably $C_1$-$C_3$ alkoxy groups, nitro groups, $C_1$-$C_3$ alkyl groups, hydroxy groups and halogen atoms), for example the benzyl, p-methoxybenzyl, o-nitrobenzyl and p-nitrobenzyl esters; benzhydryl esters; (5-methyl-2-oxo-1,3-dioxolen-4-yl)methyl esters; and phthalidyl esters.

The compounds of formula (I) are also capable of forming external acid-addition salts. As with the salts and esters defined above, the nature of the acids employed to form these salts is not critical and is only limited, where the compounds of the invention are intended for pharmaceutical use, by the requirement that the resulting acid-addition salts should be pharmaceutically acceptable. Accordingly, a wide range of acids can be employed to form such acid-addition salts. Examples include: such mineral acids as hydrochloric acid and hydrobromic acid; and such organic acids as oxalic acid, tartaric acid, citric acid, maleic acid and succinic acid. Hydrochloric acid is preferred.

The compounds of formula (I) can also form salts with a wide variety of cations. Examples of salts which may be employed in the present invention include: metal salts, particularly alkali metal or alkaline earth metal salts, such as the lithium, sodium, potassium, calcium or magnesium salts; salts with basic amino acids, such as lysine or arginine; ammonium salts; and salts with organic amines, such as cyclohexylamine, diisopropylamine or triethylamine. Of these, the alkali metal, particularly sodium and potassium, salts are preferred.

The compounds of the present invention can exist in the form of various optical isomers and stereoisomers, due to the presence of asymmetric carbon atoms. Although all of these isomers are represented herein by a single formula, it should be understood that the present invention embraces the individual isolated isomers as well as mixtures of isomers. In general, the preferred isomers are those having the (5R,6S) configuration or (in the case of compounds substituted with methyl at the 1-position) having the (1R,5S,6S) configuration. The hydroxy group at the $\alpha$-position of the 6-substituent is preferably in the R-configuration.

Examples of preferred compounds of formula (I) are given in the following Table 1, defined in terms of the substituents X and Y. The preparation of compounds 1-4, 9, 10, 15-22 and 25-29 is illustrated hereinafter in the Examples, where these compounds are referred to by the numbers used in Table 1 and where the configuration of the individual isomers is specified. For the other compounds in Table 1, the configuration of substituents is not specified and each of the compounds may be in any of the possible configurations, or may be a mixture of isomers. However, the listed compounds preferably have the (5R,6S) or (1R,5S,6S) configuration, and the hydroxy group at the α-position of the 6-substituent is preferably in the R-configuration, as already described.

TABLE 1

| Cpd. No. | X | Y |
|---|---|---|
| 1 | H | 3-oxopiperazin-1-yl |
| 2 | CH₃ | 3-oxopiperazin-1-yl |
| 3 | H | 4-methyl-3-oxopiperazin-1-yl |
| 4 | CH₃ | 4-methyl-3-oxopiperazin-1-yl |
| 5 | H | 4-acetyl-3-oxopiperazin-1-yl |
| 6 | CH₃ | 4-acetyl-3-oxopiperazin-1-yl |
| 7 | H | 3-oxo-4-mesylpiperazin-1-yl |
| 8 | CH₃ | 3-oxo-4-mesylpiperazin-1-yl |
| 9 | H | 3,5-dioxopiperazin-1-yl |
| 10 | CH₃ | 3,5-dioxopiperazin-1-yl |
| 11 | H | 4-methyl-3,5-dioxopiperazin-1-yl |
| 12 | CH₃ | 4-methyl-3,5-dioxopiperazin-1-yl |
| 13 | H | 3-carbamoyloxyazetidin-1-yl |
| 14 | CH₃ | 3-carbamoyloxyazetidin-1-yl |
| 15 | H | 3-carbamoyloxypyrrolidin-1-yl |
| 16 | CH₃ | 3-carbamoyloxypyrrolidin-1-yl |
| 17 | H | 2-carbamoylpyrrolidin-1-yl |
| 18 | H | 2-carbamoyl-4-hydroxypyrrolidin-1-yl |
| 19 | H | 2-carbamoyl-4-carbamoyloxypyrrolidin-1-yl |
| 20 | H | 3-carbamoylpiperidin-1-yl |
| 21 | H | 4-carbamoyloxypiperidin-1-yl |
| 22 | H | 3-carbamoyloxypiperidin-1-yl |
| 23 | H | 3-hydroxyiminoazetidin-1-yl |
| 24 | H | 3-methoxyiminoazetidin-1-yl |
| 25 | H | 3-hydroxyiminopyrrolidin-1-yl |
| 26 | H | 3-methoxyiminopyrrolidin-1-yl |
| 27 | H | 4-hydroxyiminopiperidin-1-yl |
| 28 | CH₃ | 4-hydroxyiminopiperidin-1-yl |
| 29 | H | 4-methoxyiminopiperidin-1-yl |

The most highly preferred compounds of those listed in Table 1 are those numbered 1 to 4, 9, 10, 15, 16, 27 and 28, and compound No. 2 is particularly preferred.

The compounds of formula (I) can be prepared as set out in the following reaction scheme of Process A.

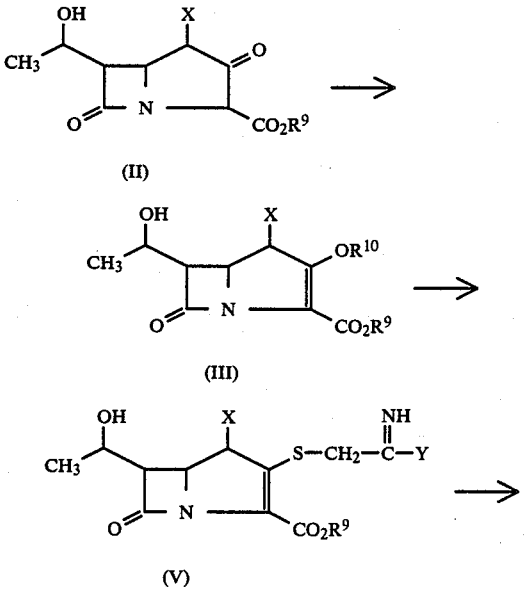

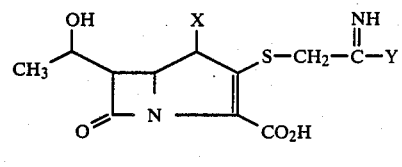

In the reaction scheme of Process A, X and Y are as defined above, and $R^9$ represents a carboxy-protecting group.

The carboxy-protecting group $R^9$ may be for example an alkyl group (such as methyl, ethyl or t-butyl), an aralkyl group (such as benzyl, diphenylmethyl, 2-nitrobenzyl or 4-nitrobenzyl), an alkenyl group (such allyl, 2-chloroallyl or 2-methylallyl), a haloalkyl group (such 2,2,2-trichloroethyl, 2,2-dibromoethyl or 2,2,2-tribromoethyl), or a 2-trimethylsilylethyl group. $R^{10}$ represents a leaving group, which may be an alkanesulfonyl group (such as methanesulfonyl, ethanesulfonyl, propanesulfonyl, isopropanesulfonyl or butanesulfonyl), an arylsulfonyl group (such as phenylsulfonyl, tolylsulfonyl or naphthylsulfonyl), a dialkylphosphoryl group (such as dimethylphosphoryl, diethylphosphoryl, dipropylphosphoryl, diisopropylphosphoryl, dibutylphosphoryl or dipentylphosphoryl), or a diarylphosphoryl group (such as diphenylphosphoryl or ditolylphosphoryl).

The starting materials of formula (II) used in Process A are all compounds which are known per se.

In the first step of Process A, the compound of formula (III) is prepared by reacting the starting material of formula (II) with a reagent capable of giving the leaving group $R^{10}$. The reagent used for this may be an anhydrous alkanesulfonic acid (e.g. methanesulfonic or ethanesulfonic acid), an anhydrous arylsulfonic acid (e.g. benzenesulfonic or p-toluenesulfonic acid), a dialkylphosphoryl halide (e.g. dimethylphosphoryl chloride or diethylphosphoryl chloride), or a diarylphosphoryl halide (e.g. diphenylphosphoryl chloride or diphenylphosphoryl bromide). The preferred reagent is anhydrous p-toluenesulfonic acid or diphenylphosphoryl chloride.

The reaction is preferably effected in the presence of a base, the nature of which is not critical, provided that it has no adverse effect on the reaction or upon the reagents, in particular on the β-lactam ring. It is preferred to use an organic base such as triethylamine or diisopropylethylamine, or an inorganic base such as potassium carbonate or sodium carbonate. It is also preferred to carry out the reaction in the presence of an inert solvent, the nature of which is likewise not critical, provided that it has no adverse effect upon the reaction. The solvent may suitably be a halogenated hydrocarbon (such as methylene chloride, 1,2-dichloroethane or chloroform), a nitrile (such as acetonitrile), or an amide (such as N,N-dimethylformamide or N,N-dimethylacetamide). The reaction can be carried out over a wide range of temperatures, but it is preferred to employ a relatively low temperature in order to inhibit the occurrence of side reactions, and a temperature of from −20° C. to 40° C. is usually employed. The time required for the reaction will vary, depending mainly on the reaction temperature and the nature of the reagents, but a period of from about 10 minutes to 5 hours will normally suffice.

The resulting compound of formula (III) can be used in the next step of Process A without isolating it from the reaction mixture. In this step, the compound of formula (V) is prepared by reacting the compound of formula (III) with a mercaptan of formula

wherein Y is as defined above. This reaction is preferably carried out in the presence of a base and of an inert solvent, such as those already mentioned in connection with the previous reaction step. The reaction temperature used will normally be in the range of from about 31 20° C. to room temperature, although this is not particularly critical; and the time required for the reaction will generally be from about 30 minutes to 8 hours.

After completion of this reaction, the resulting product of formula (V) may, if desired, be recovered from the reaction mixture by conventional means. For example, one suitable procedure comprises evaporating off the solvent from the reaction solution or mixture, adding a water-immiscible organic solvent to the residue, washing the resulting mixture with water and, if necessary, drying it, and finally evaporating off the solvent to give the desired product. If necessary, the resulting product may be further purified by a variety of conventional techniques adapted to the precise nature of the product, such as recrystallization, reprecipitation, or the various chromatographic techniques, for example column chromatography or preparative thin layer chromatography.

Alternatively, the product of formula (V) can be subjected to the final reaction step of Process A without isolating it from the reaction mixture.

The final reaction step of process A comprises the removal of the carboxy-protecting group $R^9$ from the compound of formula (V), to give the corresponding carboxylic acid of formula (I). This step is optional, and it will be appreciated that the removal of the carboxy-protecting group may not always be necessary or desired, for example when the compound of formula (V) is a pharmaceutically acceptable ester within the scope of the present invention. If it is desired to remove the carboxy-protecting group, this may be done by the use of conventional methods, the choice of which will depend upon the nature of the protecting group employed.

If the protecting group is removable by reduction, for example if it is a haloalkyl group, an aralkyl group or a benzhydryl group, it may be removed by contact with a reducing agent. In the case of haloalkyl groups, such as the 2,2-dibromoethyl or 2,2,2-trichloroethyl groups, the preferred reducing agent is a combination of zinc with acetic acid. If the protecting group is an aralkyl group (such as a benzyl or p-nitrobenzyl group) or a benzhydryl group, it is preferred to remove it either by catalytic reduction using hydrogen and a suitable catalyst, such as platinum or palladium on carbon; or by reduction with an alkali metal sulfide, such as sodium sulfide or potassium sulfide. Whatever the reduction technique, the reduction process is preferably effected in the presence of a solvent, the nature of which is not critical, provided that it has no adverse effect upon the reaction. Suitable solvents include alcohols (such as methanol or ethanol), ethers (such as tetrahydrofuran or dioxane), aliphatic carboxylic acids (such as acetic acid), or a mixture of one or more of these organic solvents with water. The reaction temperature is not critical but will normally be in the range from 0° C. to room temperature. The time required for the reaction will vary, depending upon the nature of the starting materials and reducing agents, as well as upon the reaction temperature, but a period of from 5 minutes to 12 hours will normally suffice.

After completion of the reaction, the desired compound, which will contain a free carboxy group, may be recovered by conventional means from the reaction mixture. For example, a suitable recovery technique comprises: separating off any insolubles; and then distilling off the solvent to give the desired product. This may, if necessary, be further purified by conventional means, for example recrystallization or the various chromatography techniques, such as preparative thin layer chromatography or column chromatography.

The compounds of formula (I) can alternatively be prepared as set out in the following reaction scheme of Process B:

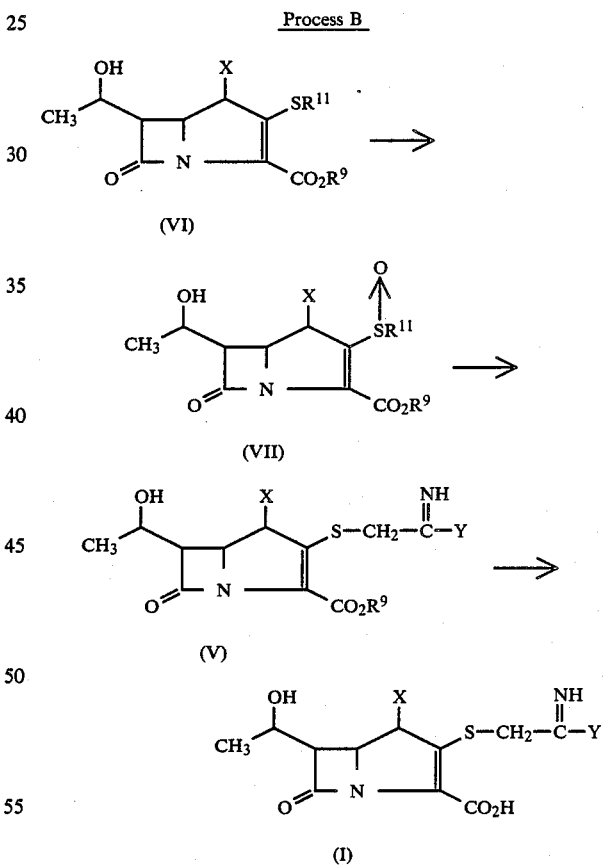

wherein $R^9$, X and Y are as defined above. $R^{11}$ represents a $C_{1-6}$ alkyl group (e.g. methyl, ethyl, propyl or isopropyl), a $C_{1-6}$ haloalkyl group (e.g. fluoromethyl, chloromethyl, fluoroethyl, chloroethyl, fluoropropyl, difluoromethyl, difluoroethyl, dichloroethyl, trifluoromethyl or trifluoroethyl), a 2-acetylaminoethyl group, a 2-acetylaminovinyl group, a $C_{6-10}$ aryl group (e.g. phenyl or naphthyl) which may optionally be substituted with up to three substituents, or a 5–10 membered mono- or bicyclic heteroaryl group containing at least one hetero-atom selected from N, S and O (e.g. pyridine or pyrimidine) which may be optionally substituted with up to three substituents. The optional substituents on the aryl group may be the same or different and are selected from halogen atoms (e.g. fluorine, chlorine or bromine), and $C_{1-6}$ alkyl (e.g. methyl, ethyl, propyl or isopropyl), $C_{1-6}$ alkoxy (e.g. methoxy, ethoxy, propoxy or isopropoxy), $C_{1-6}$ alkoxycarbonyl (e.g. methoxycarbonyl, ethoxycarbonyl or t-butoxycarbonyl), nitro, hydroxy and cyano groups. The optional substituents on the heteroaryl group may be the same or different and are selected from halogen atoms (e.g. fluorine, chlorine or bromine) and $C_{1-6}$ alkyl groups (e.g. methyl, ethyl, propyl or isopropyl).

The starting materials of formula (VI), used in Process B, can be synthesized by the methods disclosed in the published European Patent Specifications No. EP-A-71908 and No. EP-A-102239.

In the first step of Process B, the compound of formula (VI) is oxidized to the compound of formula (VII). This oxidation can be effected by reacting the compound of formula (VI) with about 1.0 to 1.5 equivalents of hydrogen peroxide, or a peracid such as peracetic acid, trifluoroperacetic acid, perbenzoic acid or 3-chloroperbenzoic acid. The reaction can suitably be carried out at a temperature of from about −40° to 50° C., with a reaction time of from about 0.5 to 24 hours, in a solvent such as methylene chloride, chloroform, 1,2-dichloroethane, methanol, ethanol, acetic acid, water, or a mixture of such solvents. If desired, the resulting product of formula (VII) can be isolated and purified by conventional techniques.

In the next reaction step of Process B, the compound of formula (VIII) is prepared by reacting the compound of formula (VII) with a mercaptan of formula

$$HS-CH_2-\overset{\overset{\displaystyle NH}{\|}}{C}-Y \quad (IV)$$

wherein Y is as defined above. This reaction is preferably carried out in the presence of a base and of an inert solvent. The choice of the base and solvent, and of the other reaction conditions, may suitably be the same as for the corresponding step in Process A described above, for the production of the compound of formula (V) from the compound of formula (III). The resulting product of formula (V) may optionally be isolated from the reaction mixture and purified, in the same manner as already described above with respect to Process A.

The compound of formula (V) may also optionally be converted to the corresponding free carboxylic acid of formula (I), by removal of the carboxy-protecting group $R^9$, and the resulting product may be isolated and purified, again as described for the corresponding step in Process A.

The final product obtained by either Process A or Process B described above may, if desired, be salified and/or esterified by conventional means, to give salts and/or esters thereof, examples of such salts and esters being given previously.

The compounds provided by the invention exhibit outstanding antibacterial activity with a wide spectrum, as well as β-lactamase inhibiting activity. As assessed by the agar plate dilution method, they have been shown to be active against a wide range of pathogenic microorganisms, including both Gram-positive bacteria (such as *Staphylococcus aureus* and *Bacillus subtilis*) and Gram-negative bacteria (such as *Escherichia coli, Shigella flexneri, Klebsiella pneumoniae, Proteus vulgaris,* Serratia species e.g. *Serratia marcescens,* Enterobacter species e.g. *Enterobacter cloacae, Salmonella enteritidis* and *Pseudomonas aeruginosa*) and are thus useful for the treatment of diseases caused by such microorganisms in humans and non-human animals. Whereas thienamycin and its analogs are inactivated in vivo in mammals by dehydropeptidase I, the compounds of the invention are much more stable to this enzyme and exhibit good urinary recovery, and thus possess good biological activity. They also exhibit low toxicity when tested in laboratory animals: for example, mice survive at dosages of above 2,000 mg/kg of compounds 3, 15 and 27 from the list in Table 1 above.

Table 2 sets out the activities of six of the compounds of the present invention against various bacteria, in terms of their minimal inhibitory concentrations (μg/ml). These compounds are identified by the same numbers as used in Table 1 above.

TABLE 2

| | Minimum Inhibitory Concentrations (μg/ml) | | | | | |
|---|---|---|---|---|---|---|
| | Compound | | | | | |
| | No. 1 | No. 2 | No. 15 | No. 16 | No. 27 | No. 28 |
| *Staphylococcus aureus* 209P | ≦0.01 | ≦0.01 | ≦0.01 | ≦0.01 | ≦0.01 | ≦0.01 |
| *Staphylococcus aureus* 56 | 0.05 | 0.05 | 0.02 | 0.05 | 0.02 | 0.05 |
| *Escherichia coli* NIHJ | 0.1 | 0.02 | 0.1 | 0.05 | 0.1 | 0.02 |
| *Escherichia coli* 609 | 0.4 | 0.05 | 0.1 | 0.1 | 0.1 | 0.1 |
| *Salmonella enteritidis* | 0.1 | 0.05 | — | — | — | — |
| *Klebsiella pneumoniae* 806 | 0.2 | 0.02 | 0.1 | 0.05 | 0.1 | 0.05 |
| *Klebsiella pneumoniae* 846 | 0.1 | 0.05 | 0.05 | 0.1 | 0.05 | 0.05 |
| *Enterobacter cloacae* 963 | 0.8 | 0.4 | 1.5 | 0.8 | 0.8 | 0.4 |
| *Serratia marcescens* 1184 | 0.2 | 0.1 | 0.1 | 0.1 | 0.1 | 0.1 |
| *Proteus vulgaris* 1420 | 1.5 | 0.4 | 1.5 | 3.1 | 0.8 | 1.5 |

In the compounds used in Table 2, compounds 1, 15 and 27 have the (5R,6S) configuration, and compounds 2, 16 and 28 have the (1R,5S,6S) configuration. In all six of the compounds, the configuration of the hydroxy group in the side-chain at position 6 is (1R).

The compounds of the invention may be administered either orally or parenterally for the treatment of diseases in humans and other animals caused by pathogenic microorganisms. The compounds may be formulated into any conventional forms for administration. For example, for oral administration, suitable formulations include tablets, granules, capsules, powders and syrups, whilst formulations for parenteral administration include injectable solutions for intramuscular or, more preferably intravenous, injection.

The compounds of the invention are preferably administered parenterally, particularly in the form of an intravenous injection.

The dose of the compound of the invention will vary, depending upon the age, body weight and condition of the patient, as well as upon the form and times of administration. However, in general the adult daily dose is from 100 to 3000 mg of the compound, which may be administered in a single dose or in divided doses.

The preparation of the compounds of the invention and of intermediates used in making them is further illustrated by the following non-limiting Examples and Preparations. The compounds of the invention are identified in the Examples by the same numbers as used in Table 1 hereinabove.

EXAMPLE 1

(5R,6S)-2-{2-[(3R)-3-Carbamoyloxypyrrolidin-1-yl]-2-iminoethylthio}-6-[(1R)-1-hydroxyethyl]-1-carbapen-2-em-3-carboxylic acid (Compound No. 15)

(1) 2-[(3R)-3-Carbamoyloxypyrrolidin-1-yl]-2-iminoethylchloride hydrochloride 0.646 ml of chloroacetonitrile was added to a solution of 23 mg of metallic sodium in 8 ml of absolute methanol, the mixture was stirred for about 60 minutes at room temperature, 1.70 g of (3R)-3-carbamoyloxypyrrolidine hydrochloride were then added, and the mixture was stirred for a further 3 hours. After completion of the reaction, a small amount of insoluble material was filtered off and the solvent was stripped off from the filtrate. Ether was added to the residue, and the precipitated crystals were collected by filtration and washed with ether, giving 2.20 g of 2-[(3R)-3-carbamoyloxypyrrolidin-1-yl]-2-iminoethylchloride hydrochloride.

NMR Spectrum (60 MHz, $D_2O$) δ ppm: 2.01–2.55 (2H, multiplet); 3.48–4.03 (4H, multiplet); 4.66 (2H, singlet); 5.08–5.44 (1H, multiplet).

(2) 2-[(3R)-3-Carbamoyloxypyrrolidin-1-yl]-2-iminoethylmercaptan hydrochloride 0.945 g of trisodium phosphorothioate were added to a solution of 1.21 g of 2-[(3R)-3-carbamoyloxypyrrolidin-1-yl]-2-iminoethylchloride hydrochloride in 8 ml of water, kept cooled in ice-water, and the mixture was stirred for about 3 hours at room temperature. After adding 6 ml of 1N hydrochloric acid, the mixture was heated to 50° C. for 30 minutes, and the solvent was then distilled off under reduced pressure. The concentrate was mixed with 8 ml of methanol, insolubles were filtered off, and the filtrate was concentrated under reduced pressure. The concentrate was crystallized by adding ether, and the crystals were collected by filtration and washed with ether, giving 1.25 g of 2-[(3R)-3-carbamoyloxypyrrolidin-1-yl]-2-iminoethylmercaptan hydrochloride.

NMR Spectrum (60 MHz, $D_2O$) δ ppm: 2.00–2.54 (2H, multiplet); 3.41–4.15 (6H, multiplet); 5.06–5.47 (1H, multiplet).

(3) (5R,6S)-2-{2-[(3R)-3-Carbamoyloxypyrrolidin-1-yl]-2-iminoethylthio}-6-[(1R)-1-hydroxyethyl]-1-carbapen-2-em-3-carboxylic acid 0.183 ml of diisopropylethylamine and 0.218 ml of diphenylphosphoryl chloride were added dropwise to an ice-cooled solution of 348 mg of p-nitrobenzyl (5R,6S)-6-[(1R)-1-hydroxyethyl]-2-oxo-1-carbapenam-3-carboxylate in 5 ml of anhydrous acetonitrile, and the mixture was stirred for 60 minutes with ice-cooling. A solution of 0.183 ml of diisopropylethylamine and 380 mg of 2-[(3R)-3-carbamoyloxypyrrolidin-1-yl]-2-iminoethylmercaptan hydrochloride in 2.5 ml of dimethylsulfoxide was then added dropwise, and the resulting mixture was stirred for a further 30 minutes with ice-cooling. The reaction mixture was poured into 200 ml of anhydrous ether, and the solvent was decanted off from the gummy material which formed. This material was dissolved in a mixture of 35 ml of tetrahydrofuran and 35 ml of 0.1M phosphate buffer (pH 7.0), and the solution was subjected to catalytic hydrogenation for 3 hours at room temperature in the presence of 0.55 g of 10% palladium-carbon. The hydrogenated solution was filtered over "Celite" (Trade Mark) filter aid, and the filtrate was extracted with 80 ml of ether. The aqueous layer was concentrated under reduced pressure, and the concentrate was subjected to chromatography through a 160 ml of column of "Dowex 50W" (Trade Mark) cation exchange resin ($Na^+$ type), giving 70 mg of the title product from the fraction eluted with water.

UV Spectrum $\lambda_{max}^{H_2O}$ nm (ε): 293.7 (7260).

NMR Spectrum (270 MHz, $D_2O$) δ ppm: 1.09 (3H, doublet, J=6.6 Hz); 2.04–2.20 (2H, multiplet) 2.82–3.04 (2H, multiplet); 3.25 (1H, doublet of doublets, J=6.2, 2.7 Hz); 3.43–4.07 (8H, multiplet); 5.11–5.19 (1H, multiplet).

EXAMPLE 2

(5R,6S)-2-[2-(4-Hydroxyiminopiperidin-1-yl)-2-iminoethylthio]-6-[(1R)-1-hydroxyethyl]-1-carbapen-2-em-3-carboxylic acid (Compound No. 27)

(1) 2-(4-Hydroxyiminopiperidin-1-yl)-2-iminoethylchloride hydrochloride 0.63 ml of chloroacetonitrile was added to a solution of 23 mg of metallic sodium in 4 ml of absolute methanol, and the mixture was stirred for about 30 minutes at room temperature. 1.5 g of 4-hydroxyiminopiperidine hydrochloride were then added and the stirring was continued for 2 hours, during which time a precipitate separated out. 25 ml of anhydrous ether were added to the reaction mixture, and the precipitated crystals were collected by filtration and washed with ether, giving 2.22 g of 2-(4-hydroxyiminopiperidin-1-yl)-2-iminoethylchloride hydrochloride.

NMR Spectrum (60 MHz, $D_2O$) δ ppm: 2.43–3.01 (4H, multiplet); 3.18–4.12 (4H, multiplet); 4.44, 4.57 (2H, singlet).

(2) 2-(4-Hydroxyiminopiperidin-1-yl)-2-iminoethylmercaptan hydrochloride 1.77 g of trisodium phosphorothioate were added to an ice-cooled solution of 2.1 g of 2-(4-hydroxyiminopiperidin-1-yl)-2-iminoethylchloride hydrochloride in 12 ml of water, the mixture was stirred at room temperature for about one hour, 9.8 ml of 1N hydrochloric acid were then added, and the mixture was heated at 65° C. for 30 minutes. The reaction mixture was concentrated under reduced pressure, the concentrate was mixed with 9.8 ml of methanol, and insolubles were filtered off. The filtrate was concentrated under reduced pressure, ether was added to the concentrate, and the crystals which separated out were collected by filtration and washed with ether, giving 1.8 g of 2-(4-hydroxyiminopiperidin-1-yl)-2-iminoethylmercaptan hydrochloride.

NMR Spectrum (60 MHz, $D_2O$) δ ppm: 2.50–2.98 (4H, multiplet); 3.49–4.00 (4H, multiplet); 3.50, 3.67 (2H, singlet).

(3) (5R,6S)-2-[2-(4-Hydroxyiminopiperidin-1-yl)-2-iminoethylthio]-6-[(1R)-1-hydroxyethyl]-1-carbapen-2-em-3-carboxylic acid 0.21 ml of diisopropylethylamine and 0.22 ml of diphenylphosphoryl chloride were added dropwise to an ice-cooled solution of 363 mg of p-nitrobenzyl (5R,6S)-6-[(1R)-1-hydroxyethyl]-2-oxo-1-carbapenam-3-carboxylate in 5 ml of anhydrous acetonitrile, and the mixture was stirred for one hour with ice-cooling. A solution of 0.18 ml of diisopropylethylamine and 324 mg of 2-(4-hydroxyiminopiperidin-1-yl)-2-iminoethylmercaptan hydrochloride in 3 ml of dimethylsulfoxide was then added dropwise to the mixture, which was stirred for a further 20 minutes with ice-cooling. The reaction mixture was then poured into 100 ml of anhydrous ether, and the solvent was decanted off from the gummy material which formed. This material was dissolved in a mixture of 20 ml of tetrahydrofuran, 7 ml of water and 23 ml of 0.1M phosphate buffer (pH 7.0), and the solution was subjected to catalytic hydrogenation at room temperature for 4 hours in the presence of 0.3 g of 10% palladium-carbon. The hydrogenated solution was filtered over "Celite" (Trade Mark) filter aid, the filtrate was extracted with 200 ml of ether, and the aqueous layer was concentrated under reduced pressure. The concentrate was subjected to chromatography using a 300 ml column of "Dowex 50W" (Trade Mark) cation exchange resin ($Na^+$ type), and 27 mg of the title compound were obtained from the fraction eluted with water.

UV Spectrum $\lambda_{max}^{H2O}$ nm: 295.

NMR Spectrum (270 MHz, $D_2O$) δ ppm: 1.09 (3H, doublet, J=6.3 Hz); 2.51–2.57 (2H, multiplet); 2.63–2.70 (2H, multiplet); 2.85–3.04 (2H, multiplet); 3.26 (1H, doublet of doublets, J=5.9, 2.1 Hz); 3.45–4.16 (8H, multiplet).

EXAMPLE 3

(5R,6S)-2-[2-(4-Methoxyiminopiperidin-1-yl)-2-iminoethylthio]-6-[(1R)-1-hydroxyethyl]-1-carbapen-2-em-3-carboxylic acid (Compound No. 29)

(1) 2-(4-Methoxyiminopiperidin-1-yl)-2-iminoethylchloride hydrochloride 2 ml of a methanolic solution containing 1.064 g of 4-methoxyiminopiperidine was added to a solution of 1.195 g of methyl 2-chloroacetimidate hydrochloride in 4 ml of absolute methanol, and the mixture was stirred at room temperature for 2 hours. After completion of the reaction, the solvent was distilled off and the concentrate was mixed with anhydrous ether. The crystals which separated out were collected by filtration and washed with ether, giving 1.5 g of 2-(4-methoxyiminopiperidin-1-yl)-2-iminoethylchloride hydrochloride.

NMR Spectrum (60 MHz, $D_2O$) δ ppm: 2.50–3.02 (4H, multiplet); 3.25–4.07 (4H, multiplet); 3.86 (3H, singlet); 4.57 (2H, singlet).

(2) 2-(4-Methoxyiminopiperidin-1-yl)-2-iminoethylmercaptan hydrochloride 1.03 g of trisodium phosphorothioate was added to a solution of 1.472 g of 2-(4-methoxyiminopiperidin-1-yl)-2-iminoethylchloride hydrochloride in 7 ml of water, kept cooled in ice-water, and the mixture was stirred at room temperature for about one hour. 5.7 ml of 1N hydrochloric acid were then added, followed by heating at 65° C. for 30 minutes. The resulting solution was concentrated under reduced pressure, mixed with ether, filtered to remove insolubles, and the filtrate concentrated under reduced pressure. The concentrate was mixed with isopropanol, and the crystals which separated out were collected by filtration and reprecipitated from a mixture of ethanol and ether, giving 850 mg of 2-(4-methoxyiminopiperidin-1-yl)-2-iminoethylmercaptan hydrochloride.

NMR Spectrum (60 MHz, $D_2O$) δ ppm: 2.46–2.98 (4H, multiplet); 3.20–4.00 (4H, multiplet); 3.68 (2H, singlet); 3.82 (3H, singlet).

(3) (5R,6S)-2-[2-(4-Methoxyiminopiperidin-1-yl)-2-iminoethylthio]-6-[(1R)-1-hydroxyethyl]-1-carbapen-2-em-3-carboxylic acid 0.22 ml of diisopropylethylamine and 0.21 ml of diphenylphosphoryl chloride was added dropwise to an ice-cooled solution of 363 mg of p-nitrobenzyl (5R, 6S)-6-[(1R)-1-hydroxyethyl]-2-oxo-1-carbapenam-3-carboxylate in 5 ml of anhydrous acetonitrile, and the mixture was stirred for one hour with ice-cooling. A solution of 0.18 ml of diisopropylethylamine and 394 mg of 2-(4-methoxyiminopiperidin-1-yl)-2-iminoethylmercaptan hydrochloride in 3 ml of dimethylsulfoxide was then added dropwise to the mixture, which was stirred for a further 20 minutes with ice-cooling. The reaction mixture was poured into 100 ml of anhydrous ether, and the solvent was decanted off from the gummy material which formed. This material was dissolved in a mixture of 20 ml of tetrahydrofuran, 7 ml of water and 23 ml of 0.1M phosphate buffer (pH 7.0), and the solution was subjected to catalytic hydrogenation at room temperature for 3 hours in the presence of 0.3 g of 10% palladium-carbon. The product was worked up and purified in the same manner as in Example 2, giving 18 mg of the title compound.

IR Spectrum $\nu_{max}^{KBr}$ cm$^{-1}$: 3370, 1763, 1695, 1590.
UV Spectrum $\lambda_{max}^{H2O}$ nm: 293.
NMR Spectrum (270 MHz, $D_2O$) δ ppm: 1.08 (3H, doublet, J=6.2 Hz); 2.40–2.80 (4H, multiplet); 2.84–3.04 (2H, multiplet); 3.24 (1H, doublet of doublets, J=6.0, 2.7 Hz); 3.16–3.80 (4H, multiplet); 3.66 (3H, singlet); 3.87–4.20 (4H, multiplet).

EXAMPLE 4

(5R,6S)-2-[2-(3-Methoxyiminopyrrolidin-1-yl)-2-iminoethylthio]-6-[(1R)-1-hydroxyethyl]-1-carbapen-2-em-3-carboxylic acid (Compound No. 26)

(1) 2-(3-Methoxyiminopyrrolidin-1-yl)-2-iminoethylchloride hydrochloride 0.63 ml of chloroacetonitrile was added to a solution of 23 mg of metallic sodium in 4 ml of absolute methanol, the mixture was stirred at room temperature for about 30 minutes, then 1.5 g of 3-methoxyiminopyrrolidine hydrochloride were added and the resulting mixture stirred for a further 2 hours. After completion of the reaction, the solvent was distilled off and the concentrate mixed with anhydrous ether. The crystals which separated out were collected by filtration and washed with ether, giving 2.2 g of 2-(3-methoxyiminopyrrolidin-1-yl)-2-iminoethylchloride hydrochloride.

NMR Spectrum (60 MHz, $D_2O$) δ ppm: 2.96 (2H, triplet, J=7 Hz); 3.43–4.56 (8H, multiplet); 3.87 (3H, singlet).

(2) 2-(3-Methoxyiminopyrrolidin-1-yl)-2-iminoethylmercaptan hydrochloride 1.77 g of trisodium phosphorothioate were added to an ice-cooled solution of 2.1 g of 2-(3-methoxyiminopyrrolidin-1-yl)-2-iminoethylchloride hydrochloride in 12 ml of water, and the mixture was stirred at room temperature for about one hour. 9.8 ml of 1N hydrochloric acid were then added, and the mixture was heated at 65° C. for 30 minutes. The resulting solution was concentrated under reduced pressure, the concentrate was mixed with 9.8 ml of isopropanol, insolubles were filtered off, and the filtrate was concentrated under reduced pressure. Ether was added to the concentrate, and the crystals which separated out were collected by filtration and reprecipitated from a mixture of ethanol and ether, giving 1.6 g of 2-(3-methoxyiminopyrrolidin-1-yl)-2-iminoethylmercaptan hydrochloride.

NMR Spectrum (60 MHz, D$_2$O) δ ppm: 3.00 (2H, triplet, J=7.0 Hz); 3.41–4.48 (8H, multiplet); 3.90 (3H, singlet).

(3) (5R,6S)-2-[2-(3-Methoxyiminopyrrolidin-1-yl)-2-iminoethylthio]-6-[(1R)-1-hydroxyethyl]-1-carbapen-2-em-3-carboxylic acid 0.21 ml of diisopropylethylamine and 0.22 ml of diphenylphosphoryl chloride were added dropwise to an ice-cooled solution of 363 mg of p-nitrobenzyl (5R,6S)-6-[(1R)-1-hydroxyethyl]-2-oxo-1-carbapenam-3-carboxylate in 5 ml of anhydrous acetonitrile, and the mixture was stirred for one hour with ice-cooling. A solution of 0.18 ml of diisopropylethylamine and 307 mg of 2-(3-methoxyiminopyrrolidin-1-yl)-2-iminoethylmercaptan hydrochloride in 3 ml of dimethylsulfoxide was then added dropwise, and the mixture was stirred for a further 20 minutes with ice-cooling. The reaction mixture was poured into 100 ml of anhydrous ether, and the solvent was decanted off from the gummy material which formed. This material was dissolved in a mixture of 20 ml of tetrahydrofuran, 7 ml of water and 23 ml of 0.1M phosphate buffer (pH 7.0), and the solution was subjected to catalytic hydrogenation at room temperature for 2 hours in the presence of 0.3 g of 10% palladium-carbon. The product was worked up and purified in the same manner as in Example 2, giving 23 mg of the title compound.

UV Spectrum $\lambda_{max}^{H2O}$ nm: 294.

NMR Spectrum (270 MHz, D$_2$O) δ ppm: 1.08 (3H, doublet, J=6.2 Hz); 2.66–3.15 (4H, multiplet); 3.16–4.20 (11H, multiplet); 3.24 (1H, doublet of doublets, J=5.9, 2.6 Hz).

EXAMPLE 5

(5R,6S)-2-[2-(3-Hydroxyiminopyrrolidin-1-yl)-2-iminoethylthio]-6-[(1R)-1-hydroxyethyl]-1-carbapen-2-em-3-carboxylic acid (Compound No. 25)

(1) 2-(3-Hydroxyiminopyrrolidin-1-yl)-2-iminoethylchloride hydrochloride 0.44 ml of chloroacetonitrile was added to a solution of sodium methoxide, prepared by dissolving 16 mg of metallic sodium in 2.8 ml of absolute methanol, and the mixture was stirred at room temperature for about 30 minutes. 950 mg of 3-hydroxyiminopyrrolidine hydrochloride were then added, and the mixture was stirred for a further 2 hours. After completion of the reaction, the solvent was distilled off and the concentrate mixed with anhydrous ether, giving a crystalline product. The crystals were collected by filtration and washed with ether, giving 1.15 g of 2-(3-hydroxyiminopyrrolidin-1-yl)-2-iminoethylchloride hydrochloride.

NMR Spectrum (60 MHz, D$_2$O) δ ppm: 2.94 (2H, triplet, J=7.0 Hz); 3.42–4.26 (4H, multiplet); 4.38, 4.43 (2H, singlet).

(2) 2-(3-Hydroxyiminopyrrolidin-1-yl)-2-iminoethylmercaptan hydrochloride 945 mg of trisodium phosphorothioate were added to a solution of 1.05 g of 2-(3-hydroxyiminopyrrolidin-1-yl)-2-iminoethylchloride hydrochloride in 6.4 ml of water, cooled with ice-water, and the mixture was stirred at room temperature for about one hour. 5.2 ml of 1N hydrochloric acid were added, and the mixture was heated at 65° C. for 30 minutes and then concentrated under reduced pressure. The concentrate was mixed with 5.2 ml of methanol, insolubles were filtered off, and the filtrate was concentrated under reduced pressure. Anhydrous ether was added to the concentrate, and the precipitated crystals were collected by filtration and washed with ether, giving 670 mg of 2-(3-hydroxyiminopyrrolidin-1-yl)-2-iminoethylmercaptan hydrochloride.

NMR Spectrum (60 MHz, D$_2$O) δ ppm: 2.91 (2H, triplet, J=7.0 Hz); 3.34–4.35 (6H, multiplet).

(3) (5R,6S)-2-[2-(3-Hydroxyiminopyrrolidin-1-yl)-2-iminoethylthio]-6-[(1R)-1-hydroxyethyl]-1-carbapen-2-em-3-carboxylic acid 0.21 ml of diisopropylethylamine and 0.22 ml of diphenylphosphoryl chloride were added dropwise to an ice-cooled solution of 363 mg of p-nitrobenzyl (5R,6S)-6-[(1R)-1-hydroxyethyl]-2-oxo-1-carbapenam-3-carboxylate in 5 ml of anhydrous acetonitrile, and the solution was stirred for one hour with ice-cooling. A solution of 0.18 ml of diisopropylethylamine and 282 mg of 2-(3-hydroxyiminopyrrolidin-1-yl)-2-iminoethylmercaptan hydrochloride in 3 ml of dimethylsulfoxide was added, and the mixture was then stirred for a further 20 minutes with ice-cooling. The reaction mixture was poured into 100 ml of anhydrous ether, and the solvent was decanted off from the gummy material which formed. This material was dissolved in a mixture of 20 ml of tetrahydrofuran, 7 ml of water and 23 ml of 0.1M phosphate buffer (pH 7.0), and the solution was catalytically hydrogenated at room temperature for 2 hours in the presence of 0.3 g of 10% palladium-carbon. The product was worked up and purified in the same manner as in Example 2, giving 15 mg of the title compound.

UV Spectrum $\lambda_{max}^{H2O}$ nm: 294.

NMR Spectrum (270 MHz, D$_2$O) δ ppm: 1.08 (3H, doublet, J=6.2 Hz); 2.71–3.02 (2H, multiplet); 3.24 (1H, doublet of doublets, J=6.2, 2.6 Hz); 3.99–4.21 (8H, multiplet).

EXAMPLE 6

(5R,6S)-2-[2-(4-Carbamoyloxypiperidin-1-yl)-2-iminoethylthio]-6-[(1R)-1-hydroxyethyl]-1-carbapen-2-em-3-carboxylic acid (Compound No. 21)

(1) 2-(4-Carbamoyloxypiperidin-1-yl)-2-iminoethylchloride hydrochloride 5.29 ml of chloroacetonitrile were added to a solution of 192 mg of metallic sodium in 80 ml of anhydrous methanol, and the mixture was stirred at room temperature for one hour. 15.10 g of 4-carbamoyloxypiperidine hydrochloride were than added, and the mixture was stirred for a further 2 hours. The reaction mixture was worked up in the same manner as in Example 1(1), giving 21.00 g of 2-(4-carbamoyloxypiperidin-1-yl)-2-iminoethylchloride hydrochloride.

NMR Spectrum (60 MHz, D$_2$O) δ ppm: 1.64–2.32 (4H, multiplet); 3.40–4.98 (4H, multiplet); 4.54 (2H, singlet); 4.41–5.31 (1H, multiplet).

(2) 2-(4-Carbamoyloxypiperidin-1-yl)-2-iminoethylmercaptan hydrochloride 4.95 g of trisodium phosphorothioate were added to an ice-cooled solution of 6.40 g of 2-(4-carbamoyloxypiperidin-1-yl)-2-iminoethylchloride hydrochloride in 32 ml of water, and the mixture was stirred at room temperature for 2.5 hours. 28 ml of 1N hydrochloric acid were then added, and the mixture was heated at 60°

C. for 30 minutes. The reaction mixture was worked up in the same manner as in Example 1(2), giving 6.20 g of 2-(4-carbamoyloxypiperidin-1-yl)-2-iminoethylmercaptan hydrochloride.

NMR Spectrum (60 MHz, D$_2$O) δ ppm: 1.63-2.29 (4H, multiplet); 3.40-3.98 (6H, multiplet); 4.51-5.10 (1H, multiplet).

(3) (5R,6S)-2-[2-(4-Carbamoyloxypiperidin-1-yl)-2-iminoethylthio]-6-[(1R)-1-hydroxyethyl]-1-carbapen-2-em-3-carboxylic acid 1.83 ml of diisopropylethylamine and 2.18 ml of diphenylphosphoryl chloride were added dropwise to an ice-cooled solution of 3.48 g of 4-nitrobenzyl (5R,6S)-6-[(1R)-1-hydroxyethyl]-2-oxo-1-carbapenam-3-carboxylate in 20 ml of anhydrous acetonitrile, and the mixture was stirred for one hour with ice-cooling. The reaction mixture was then added to a mixture of 2.1 ml of diisopropylethylamine in 70 ml of tetrahydrofuran and 60 ml of 0.1M phosphate buffer solution (pH 7.0), which had been cooled with ice and salt, together with 10 ml of an aqueous solution of 3.17 g of 2-(4-carbamoyloxypiperidin-1-yl)-2-iminoethylmercaptan hydrochloride, and the resulting mixture was stirred for 5 minutes. The reaction mixture was then subjected to hydrogenation at room temperature for 2 hours, in the presence of 3.0 g of 10% palladium-carbon. The hydrogenated reaction mixture was worked up in the same manner as in Example 1(3), giving 783 mg of the title compound.

UV Spectrum $\lambda_{max}^{H_2O}$ nm (ε): 293.7 (6010).

NMR Spectrum (270 MHz, D$_2$O) δ ppm: 1.09 (3H, doublet, J=6.6 Hz); 1.64-2.01 (4H, multiplet); 2.83-3.17 (3H, multiplet); 3.26 (1H, doublet of doublets, J=5.9, 2.6 Hz); 3.35-3.70 (4H, multiplet); 3.78-4.15 (3H, multiplet); 4.74 (1H, multiplet).

EXAMPLE 7

(5R,6S)-2-{-2-[(3RS)-3-Carbamoyloxypiperidin-1-yl]-2-iminoethylthio}-6-[(1R)-1-hydroxyethyl]-1-carbapen-2-em-3-carboxylic acid (Compound No. 22)

The following intermediates and final product were prepared by following substantially the same procedures as in Example 1.

(1) 2-[(3RS)-3-Carbamoyloxypiperidin-1-yl]-2-iminoethylchloride hydrochloride

NMR Spectrum (60 MHz, D$_2$O) δ ppm: 1.42-2.27 (4H, multiplet); 3.23-4.19 (4H, multiplet); 4.52 (2H, singlet); 4.72-5.14 (1H, multiplet);

(2) 2-[(3RS)-3-Carbamoyloxypiperidin-1-yl]-2-iminoethylmercaptan hydrochloride

NMR Spectrum (60 MHz, D$_2$O) δ ppm: 1.31-2.20 (4H, multiplet); 3.12-4.17 (6H, multiplet); 4.50-5.10 (1H, multiplet).

(3) (5R,6S)-2-{2-8 (3RS)-3-Carbamoyloxypiperidin-1-yl]-2-iminoethylthio}-6-[(1R)-1-hydroxyethyl]-1-carbapen-2-em-3-carboxylic acid UV Spectrum $\lambda_{max}^{H_2O}$ nm (ε): 294.3 (6998).

NMR Spectrum (90 MHz, D$_2$O) δ ppm: 1.75 (3H, doublet, J=6.2 Hz); 2.00-2.68 (4H, multiplet); 3.41-4.93 (11H, multiplet); 5.28-5.59 (1H, multiplet).

EXAMPLE 8

(5R,6S)-2-{2-[(3RS)-3-Carbamoylpiperidin-1-yl]-2-iminoethylthio}-6-[(1R)-1-hydroxyethyl]-1-carbapen-2-em-3-carboxylic acid (Compound No. 20)

(1) 2-[(3RS)-3-Carbamoylpiperidin-1-yl]-2-iminoethylchloride hydrochloride 1.28 g of (3RS)-3-carbamoylpiperidine were added to a solution of 1.44 g of methyl 2-chloroacetimidate hydrochloride in 5 ml of anhydrous methanol, and the mixture was stirred at room temperature for 2 hours. The reaction mixture was then worked up in the same manner as in Example 3(1), giving 2.34 g of 2-[(3RS)-3-carbamoylpiperidin-1-yl]-2-iminoethylchloride hydrochloride.

NMR Spectrum (60 MHz, D$_2$O) δ ppm: 1.44-2.26 (5H, multiplet); 2.50-4.14 (4H, multiplet); 4.43, 4.53 (2H, singlet).

(2) 2-[(3RS)-3-Carbamoylpiperidin-1-yl]-2-iminoethylmercaptan hydrochloride 1.43 g of trisodium phosphorothioate were added to an ice-cooled solution of 2.04 g of 2-[(3RS)-3-carbamoylpiperidin-1-yl]-2-iminoethylchloride hydrochloride in 9.7 ml of water, and the mixture was stirred at room temperature for one hour. 7.9 ml of 1N hydrochloric acid were then added, and the mixture was heated at 50° C. for 30 minutes. The reaction mixture was then worked up in the same manner as in Example 3(2) to give 2.0 g of 2-[(3RS)-3-carbamoylpiperidin-1-yl]-2-iminoethylmercaptan hydrochloride.

NMR Spectrum (60 MHz, D$_2$O) δ ppm: 1.50-2.24 (5H, multiplet); 2.54-4.20 (4H, multiplet); 3.52, 3.65 (2H, singlet).

(3) (5R,6S)-2-{2-[(3RS)-3-Carbamoylpiperidin-1-yl]-2-iminoethylthio}-6-[(1R)-1-hydroxyethyl]-1-carbapen-2-em-3-carboxylic acid By following the procedure of Example 3(3), but using 1.03 g of 2-[(3RS)-3-carbamoylpiperidin-1-yl]-2-iminoethylmercaptan hydrochloride in 7 ml of water, 316 mg of the title compound were obtained.

UV Spectrum $\lambda_{max}^{H_2O}$ nm (ε): 294.5 (6530).

NMR Spectrum (270 MHz, D$_2$O) δ ppm: 1.10 (1H, doublet, J=6.6 Hz); 1.42-2.00 (4H, multiplet); 2.50-2.75 (1H, multiplet); 2.83-3.47 (5H, multiplet); 3.62-4.13 (5H, multiplet).

EXAMPLE 9

(5R,6S)-2-[2-(3-Oxopiperazin-1-yl)-2-iminoethylthio]-6-[(1R)-1-hydroxyethyl]-1-carbapen-2-em-3-carboxylic acid (Compound No. 1)

(1) 2-(3-Oxopiperazin-1-yl)-2-iminoethylchloride hydrochloride 8.64 g of 2-oxopiperazine were added to a solution of 12.4 g of methyl 2-chloroacetimidate hydrochloride in 44.8 ml of anhydrous methanol, and the mixture was stirred at room temperature for 2 hours. After completion of the reaction, a small amount of insoluble material was filtered off and the solvent was distilled off from the filtrate. Ether was added to the residue, and the precipitated crystals were collected by filtration and washed with ether, giving 18.0 g of 2-(3-oxopiperazin-1-yl)-2-iminoethylchloride hydrochloride.

NMR Spectrum (60 MHz, D$_2$O) δ ppm: 3.40-3.69 (2H, multiplet); 3.69-4.13 (2H, multiplet); 4.27 (2H, singlet); 4.59 (2H, singlet).

(2) 2-(3-Oxopiperazin-1-yl)-2-iminoethylmercaptan hydrochloride 12.0 g of trisodium phosphorothioate were added to a solution of 14.3 g of 2-(3-oxopiperazin-1-yl)-2-iminoethylchloride hydrochloride in 80 ml of water, kept cooled in ice-water, and the mixture was stirred at room temperature for one hour. After adding 66.5 ml of 1N hydrochloric acid, the mixture was heated to 50° C. for 30 minutes, and the solvent was then distilled off under reduced pressure. The concentrate was mixed with 200 ml of methanol, insolubles were filtered off, and the filtrate was concentrated under reduced pressure. The concentrate was crystallized by adding ether, and the crystals were collected by filtration and washed with ether, giving 6.4 g of 2-(3-oxopiperazin-1-yl)-2-iminoethylmercaptan hydrochloride.

NMR Spectrum (60 MHz, D$_2$O) δ ppm: 3.37–4.10 (4H, multiplet); 3.68 (2H, singlet); 4.18 (2H, singlet).

(3) (5R,6S)-2-[2-(3-Oxopiperazin-1-yl)-2-iminoethylthio]-6-[(1R)-1-hydroxyethyl]-1-carbapen-2-em-3-carboxylic acid 1.62 ml of diisopropylethylamine and 1.92 ml of diphenylphosphoryl chloride were added dropwise to an ice-cooled solution of 3.0 g of (5R,6S)-6-[(1R)-1-hydroxyethyl]-2-oxo-1-carbapenam-3-carboxylate in 36 ml of anhydrous acetonitrile, and the mixture was stirred for one hour with ice-cooling. The reaction mixture was then added to an ice-cooled mixture of 1.86 ml of diisopropylethylamine in 180 ml of tetrahydrofuran and 160 ml of 0.1M phosphate buffer solution (pH 7.0), together with 20 ml of an aqueous solution of 2.79 g of 2-(3-oxopiperazin-1-yl)-2-iminoethylmercaptan hydrochloride, and the resulting mixture was stirred for 50 minutes. The reaction mixture was then subjected to hydrogenation at room temperature for 2.5 hours, in the presence of 3.0 g of 10% palladium-carbon. The hydrogenated mixture was filtered over "Celite" (Trade Mark) filter aid, and the filtrate was extracted with 200 ml of ether. The aqueous layer was concentrated under reduced pressure, and the concentrate was subjected to chromatography through a 250 ml column of "Dowex 50W" (Trade Mark) cation exchange resin (Na+ type), giving 850 mg of the title product from the fraction eluted with water.

UV Spectrum $\lambda_{max}^{H_2O}$nm (ε): 293.6 (7728).

NMR Spectrum (270 MHz, D$_2$O) δ ppm: 1.09 (3H, doublet, J=6.6 Hz); 2.84–3.12 (2H, multiplet); 3.27 (1H, doublet of doublets, J=5.9, 2.9 Hz); 3.38 (2H, triplet, J=5.3 Hz); 3.52–3.90 (3H, multiplet); 3.96–4.28 (5H, multiplet).

EXAMPLE 10

(5R,6S)-2-{2-[(2S)-2-Carbamoylpyrrolidin-1-yl]-2-iminoethylthio}-6-[(1R)-1-hydroxyethyl]-1-carbapen-2-em-3-carboxylic acid (Compound No. 17)

The following intermediates and final product were obtained by substantially the same procedure as in Example 1.

(1) 2-[(2S)-Carbamoylpyrrolidin-1-yl]-2-iminoethylchloride hydrochloride

NMR Spectrum (60 MHz, D$_2$O) δ ppm: 1.67–2.62 (4H, multiplet); 3.43–4.04 (2H, multiplet); 4.42, 4.56 (2H, singlet); 4.38–5.03 (1H, multiplet).

(2) 2-[(2S)-Carbamoylpyrrolidin-1-yl]-2-iminoethylmercaptan hydrochloride

NMR Spectrum (60 MHz, D$_2$O) δ ppm: 1.58–2.66 (4H, multiplet); 3.38–4.10 (4H, multiplet); 4.39–5.05 (1H, multiplet).

(3) (5R,6S)-2-{2-[(2S)-2-Carbamoylpyrrolidin-1-yl]-2-iminoethylthio}-6-[(1R)-1-hydroxyethyl]-1-carbapen-2-em-3-carboxylic acid UV Spectrum $\lambda_{max}^{H_2O}$nm: 292.5.

EXAMPLE 11

(5R,6S)-2-{2-[(2S,4R)-2-Carbamoyl-4-hydroxypyrrolidin-1-yl]-2-iminoethylthio}-6-[(1R)-1-hydroxyethyl]-1-carbapen-2-em-3-carboxylic acid (Compound No. 18)

The following intermediates and final product were obtained by substantially the same procedure as in Example 1.

(1) 2-[(2S,4R)-2-Carbamoyl-4-hydroxypyrrolidin-1-yl]-2-iminoethylchloride hydrochloride NMR Spectrum (60 MHz, D$_2$O) δppm: 2.06–2.71 (2H, multiplet); 3.36–4.18 (2H, multiplet); 4.48 (2H, singlet); 4.29–5.31 (2H, multiplet).

(2) 2-[(2S,4R)-2-Carbamoyl-4-hydroxypyrrolidin-1-yl]-2-iminoethylmercaptan hydrochloride NMR Spectrum (60 MHz, D$_2$O) δppm: 2.01–2.81 (2H, multiplet); 3.20–4.06 (4H, multiplet); 4.42–5.03 (2H, multiplet).

(3) (5R,6S)-2-{2-[(2S,4R)-2-Carbamoyl-4-hydroxypyrrolidin-1-yl]-2-iminoethylthio}-6-[(1R)-1-hydroxyethyl]-1-carbapen-2-em-3-carboxylic acid UV Spectrum $\lambda_{max}^{H_2O}$nm: 294.

EXAMPLE 12

(5R,6S)-2-{2-[(2S,4R)-2-Carbamoyl-4-carbamoyloxypyrrolidin-1-yl]-2-iminoethylthio}-6-[(1R)-1-hydroxyethyl]-1-carbapen-2-em-3-carboxylic acid (Compound No. 19)

The following intermediates and final product were obtained by substantially the same procedure as in Example 1.

(1) 2-[(2S,4R)-2-Carbamoyl-4-carbamoyloxypyrrolidin-1-yl]-2-iminoethylchloride hydrochloride NMR Spectrum (60 MHz, D$_2$O) δppm: 2.15–3.00 (2H, multiplet); 3.76–5.58 (4H, multiplet); 4.52 (2H, singlet).

(2) 2-[(2S,4R)-2-Carbamoyl-4-carbamoyloxypyrrolidin-1-yl]-2-iminoethylmercaptan hydrochloride NMR Spectrum (60 MHz, D$_2$O) δppm: 2.08–2.92 (2H, multiplet); 3.27–4.70 (5H, multiplet); 5.13–5.44 (1H, multiplet).

(3) (5R,6S)-2-{2-[(2S,4R)-2-Carbamoyl-4-carbamoyloxypyrrolidin-1-yl]-2-iminoethylthio}-6-[(1R)-1-hydroxyethyl]-1-carbapen-2-em-3-carboxylic acid UV Spectrum $\lambda_{max}^{H_2O}$nm: 294.

EXAMPLE 13

(1R,5S,6S)-2-[2-(3-Oxopiperazin-1-yl)-2-iminoethylthio]-6-[(1R)-1-hydroxyethyl]-1-methyl-1-carbapen-2-em-3-carboxylic acid (Compound No. 2)

0.28 ml of diisopropylethylamine and 0.29 ml of diphenylphosphoryl chloride were added dropwise to an ice-cooled solution of 500 mg of 4-nitrobenzyl (1R,5R,6S)-6-[(1R)-1-hydroxyethyl]-1-methyl-2-oxo-1-carbapenam-3-carboxylate in 6 ml of anhydrous acetonitrile, after which the mixture was stirred for one hour with ice-cooling. 0.20 ml of diisopropylethylamine and a suspension of 452 mg of 2-(3-oxopiperazin-1-yl)-2-iminoethylmercaptan hydrochloride in 3.6 ml of dimethylsulfoxide were added to the reaction mixture, and the whole mixture was stirred for 30 minutes with ice-cooling. The reaction mixture was poured into 200 ml of anhydrous ether and the solvent was decanted off from the gummy material which formed. This material was dissolved in a mixture of 40 ml of tetrahydrofuran and 46 ml of 0.1M phosphate buffer (pH 7.0), and the solution was subjected to hydrogenation for 2 hours at room temperature in the presence of 662 mg of 10% palladium-carbon. The hydrogenated mixture was filtered over "Celite" (Trade Mark) filter aid, and the filtrate was extracted with 80 ml of ether. The aqueous layer was concentrated under reduced pressure, and the concentrate was subjected to chromatography through a 160 ml column of "Dowex 50W" (Trade Mark) cation exchange resin (Na+ type), giving 58 mg of the title product from the fraction eluted with water.

UV Spectrum $\lambda_{max}^{H_2O}$nm ($\epsilon$): 292.3 (6185).

NMR Spectrum (270 MHz, D$_2$O) $\delta$ppm: 1.01 (3H, doublet, J=7.3 Hz); 1.10 (3H, doublet, J=6.6 Hz); 3.10–3.27 (1H, multiplet); 3.28–4.96 (4H, multiplet); 3.55–3.90 (2H, multiplet); 3.95–4.26 (5H, multiplet).

EXAMPLE 14

(1R,5S,6S)-2-{2-[(3R)-3-Carbamoyloxypyrrolidin-1-yl]-2-iminoethylthio}-6-[(1R)-1-hydroxyethyl]-1-methyl-1-carbapen-2-em-3-carboxylic acid (Compound No. 16)

0.28 ml of diisopropylethylamine and 0.29 ml of diphenylphosphoryl chloride were added dropwise to an ice-cooled solution of 500 mg of 4-nitrobenzyl (1R,5R,6S)-6-[(1R)-1-hydroxyethyl]-1-methyl-2-oxo-1-carbapenam-3-carboxylate in 6 ml of anhydrous acetonitrile, and then the mixture was stirred for one hour with ice-cooling. 0.20 ml of diisopropylethylamine and a solution of 458 mg of 2-[(3R)-3-carbamoyloxypyrrolidin-1-yl]-2-iminoethylmercaptan hydrochloride in 3.6 ml of dimethylsulfoxide were added to the reaction mixture, and then the whole mixture was stirred for a further 30 minutes with ice-cooling. The reaction mixture was poured into 200 ml of anhydrous ether and the solvent was decanted off from the gummy material which formed. This material was dissolved in a mixture of 40 ml of tetrahydrofuran and 46 ml of 0.1M phosphate buffer (pH 7.0), and the solution was subjected to hydrogenation for 2 hours at room temperature in the presence of 0.6 g of 10% palladium-carbon. The hydrogenation mixture was filtered over "Celite" (Trade Mark) filter aid, and the filtrate was extracted with 80 ml of ether. The aqueous layer was concentrated under reduced pressure and the concentrate was subjected to chromatography through a 160 ml column of "Dowex 50W" (Trade Mark) cation exchange resin (Na+ type), giving 132 mg of the title product from the fraction eluted with water.

UV Spectrum $\lambda_{max}^{H_2O}$nm ($\epsilon$): 292.7 (7020).

NMR Spectrum (270 MHz, D$_2$O) $\epsilon$ppm: 1.00 (3H, doublet, J=7.3 Hz); 1.10 (3H, doublet, J=6.2 Hz); 2.03–2.24 (2H, multiplet); 3.15–3.23 (1H, multiplet); 3.27–3.37 (1H, multiplet); 3.38–3.54 (2H, multiplet); 3.54–3.95 (4H, multiplet); 3.97–4.15 (2H, multiplet); 5.10–5.20 (1H, multiplet).

EXAMPLE 15

(1R,5S,6S)-2-[2-(4-Hydroxyiminopiperidin-1-yl)-2-iminoethylthio]-6-[(1R)-1-hydroxyethyl]-1-methyl-1-carbapen-2-em-3-carboxylic acid (Compound No. 28)

0.28 ml of diisopropylethylamine and 0.29 ml of diphenylphosphoryl chloride were added dropwise to an ice-cooled solution of 500 mg of 4-nitrobenzyl (1R,5R,6S)-6-[(1R)-1-hydroxyethyl]-1-methyl-2-oxo-1-carbapenam-3-carboxylate in 6 ml of anhydrous acetonitrile, and then the mixture was stirred for one hour with ice-cooling. 0.2 ml of diisopropylethylamine and 426 mg of 2-(4-hydroxyiminopiperidin-1-yl)-2-iminoethylmercaptan hydrochloride in 3.6 ml of dimethylsulfoxide were added to the reaction mixture, and then the whole mixture was stirred for a further 30 minutes with ice-cooling. The reaction mixture was poured into 200 ml of anhydrous ether and the solvent was decanted off from the gummy material which formed. This material was dissolved in a mixture of 40 ml of tetrahydrofuran and 46 ml of 0.1M phosphate buffer (pH 7.0), and the solution was subjected to hydrogenation for 2 hours at room temperature in the presence of 0.6 g of 10% palladium-carbon. The hydrogenation mixture was filtered over "Celite" (Trade Mark) filter aid, and the filtrate was extracted with 80 ml of ether. The aqueous layer was concentrated under reduced pressure and the concentrate was subjected to chromatography through a 160 ml column of "Dowex 50W" (Trade Mark) cation exchange resin (Na+ type), giving 68 mg of the title product from the fraction eluted with water.

UV Spectrum $\lambda_{max}^{H_2O}$nm ($\epsilon$): 292.9 (5370).

NMR Spectrum (270 MHz, D$_2$O) $\delta$ppm: 1.01 (3H, doublet, J=7.0 Hz); 1.10 (3H, doublet, J=6.6 Hz); 2.46–2.61 (2H, multiplet); 2.61–2.77 (2H, multiplet); 3.08–3.25 (1H, multiplet); 3.34 (1H, doublet of doublets, J=2.9 6.2 Hz); 3.37–3.88 (6H, multiplet); 4.01–4.15 (2H, multiplet).

EXAMPLE 16

(5R,6S)-2-[2-(3,5-Dioxopiperazin-1-yl)-2-iminoethylthio]-6-[(1R)-1-hydroxethyl]-1-carbapen-2-em-3-carboxylic acid (Compound No. 9)

The following intermediates and final product were obtained by substantially the same procedures as in Example 3.

(1) 2-(3,5-Dioxopiperazin-1-yl)-2-iminioethylchloride hydrochloride

NMR Spectrum (60 MHz, D$_2$O) $\delta$ppm: 3.75 (4H, broad singlet); 4.45 (2H, singlet).

(2) 2-(3,5-Dioxopiperazin-1-yl)-2-iminoethylmercaptan hydrochloride

NMR Spectrum (60 MHz, D$_2$O) $\delta$ppm: 3.72–3.80 (4H, broad singlet).

(3) (5R,6S)-2-[2-(3,5-Dioxopiperazin-1-yl)-2-iminoethylthio]-6-[(1R)-1-hydroxyethyl]-1-carbapen-2-em-3-carboxylic acid UV Spectrum $\lambda_{max}^{H_2O}$nm: 293.

EXAMPLE 17

(5R,6S)-2-[2-(4-Methyl-3-oxopiperazin-1-yl)-2-iminoethylthio]-6-[(1R)-1-hydroxyethyl]-1-carbapen-2-em-3-carboxylic acid (Compound No. 3)

The following intermediates and final product were obtained by substantially the same procedures as in Example 1.

(1) 2-(4-Methyl-3-oxopiperzin-1-yl)-2-iminoethylchloride hydrochloride

NMR Spectrum (60 MHz, D$_2$O) $\delta$ppm: 2.95 (3H, singlet); 3.32–4.14 (4H, multiplet); 4.21 (2H, singlet); 4.52 (2H, singlet).

(2) 2-(4-Methyl-3-oxopiperazin-1-yl)-2-iminoethylmercaptan hydrochloride

NMR Spectrum (60 MHz, D$_2$O) $\delta$ ppm: 2.98 (3H, singlet); 3.38–4.28 (8H, multiplet).

(3) (5R,6S)-2-[2-(4-Methyl-3-oxopiperazin-1-yl)-2-iminoethylthio]-6-[(1R)-1-hydroxyethyl]-1-carbapen-2-em-3-carboxylic acid UV Spectrum $\nu_{max}^{H_2O}$ nm: 294.

NMR Spectrum (270 MHz, D₂O) δ ppm: 1.08 (3H, doublet, J=6.6 Hz); 2.85 (3H, singlet); 2.76–3.08 (2H, multiplet); 3.26 (1H, doublet of doublets, J=6.0, 2.8 Hz); 3.46 (2H, triplet, J=5.1 Hz); 3.57–4.20 (8H, multiplet).

EXAMPLE 18

(1R,5S,6S)-2-[2-(4-Methyl-3-oxopiperazin-1-yl)-2-iminoethylthio]-6-[(1R)-1-hydroxyethyl]-1-methyl-1-carbapen-2-em-3-carboxylic acid (Compound No. 4)

The procedure of Example 1(3) was repeated, except that 100 mg of p-nitrobenzyl (1R,5R,6S)-6-[(1R)-1-hydroxyethyl]-1-methyl-2-oxo-1-carbapenam-3-carboxylate and 90 mg of 2-(4-methyl-3-oxopiperazin-1-yl)-2-iminoethylmercaptan hydrochloride were used. After hydrogenation and filtration over "Celite" (Trade Mark) filter aid, the filtrate was extracted twice with 20 ml portions of diethyl ether. The aqueous phase was concentrated by evaporation under reduced pressure, and the residue was purified by chromatography through a Lobar column (Merck "LiChloprep RP-8", size B, two columns), eluted with 2% aqueous methanol, to give 10 mg of the title compound.

UV Spectrum $\lambda_{max}^{H2O}$ nm: 292.

EXAMPLE 19

(1R,5S,6S)-2-[2-(3,5-Dioxopiperazin-1-yl)-2-iminoethylthio]-6-[(1R)-1-hydroxyethyl]-1-methyl-1-carbapen-2-em-3-carboxylic acid (Compound No. 10)

The title compound was obtained by following the procedure of Example 1(3).

UV Spectrum $\lambda_{max}^{H2O}$ nm: 293.

EXAMPLE 20

(1R,5S,6S)-2-[2-(3-Oxopiperazin-1-yl)-2-iminoethylthio]-6-[(1R)-1-hydroxyethyl]-1-methyl-1-carbapen-2-em-3-carboxylic acid (Compound No. 2)

A suspension of 108 mg of 2-(3-oxopiperazin-1-yl)-2-iminoethylmercaptan hydrochloride in 0.8 ml of dimethyl sulfoxide was added, under ice-cooling, to a solution of 130 mg of p-nitrobenzyl (1RS,5S,6S)-2-phenylsulfinyl-6-[(1R)-1-hydroxyethyl]-1-methyl-1-carbapen-2-em-3-carboxylate in 1.4 ml of acetonitrile, and the mixture was stirred for 30 minutes. The reaction mixture was then poured into 50 ml of anhydrous diethyl ether, and the solvent was decanted off. The oily residue was dissolved in a mixture of 8 ml of tetrahydrofuran, 2.7 ml of water and 9.4 ml of 0.1M phosphate buffer solution (pH 7.0), and the resulting solution was subjected to catalytic hydrogenation at room temperature for 2 hours in the presence of 160 mg of palladium-carbon. The insolubles were filtered off over "Celite" (Trade Mark) filter aid, and the filtrate was extracted twice with 30 ml portions of diethyl ether. The aqueous phase was concentrated by evaporation under reduced pressure and the residue was purified through a Lobar column (Merck "LiChloprep RP-8", size B, two columns), eluted with 5% aqueous methanol, to give the title compound having the same properties as those of the product obtained in Example 13.

PREPARATION 1 p-Nitrobenzyl (1R,5S,6S)-2-phenylthio-6-[(1R)-1-hydroxyethyl]-1-methyl-1-carbapen-2-em-3-carboxylate (1) (3R,4R)-3-[(1R)-1-t-Butyldimethylsilyloxyethyl]-4-acetoxy-1-trimethylsilyl-2-azetidinone First 22.8 ml of trimethylsilyl chloride and then 25.1 ml of triethylamine were added dropwise to a solution of 43.1 g of (3R,4R)-3-[(1R)-1-t-butyldimethylsilyloxyethyl]-4-acetoxy-2-azetidinone in 450 ml of methylene chloride, maintained at 0° to 5° C. in an ice-water bath. The mixture was stirred at room temperature for 2 hous, then again cooled to 0° to 5° C. in an ice-water bath and filtered under suction. The filtrate was concentrated under reduced pressure. The residue was mixed with 300 ml of anhydrous ether and insolubles were filtered off. The solvent was stripped off from the filtrate, giving 52.8 g of crystalline (3R,4R)-3-[(1R)-1-t-butyldimethylsilyloxyethyl]-4-acetoxy-1-trimethylsilyl-2-azetidinone.

NMR spectrum (60 MHz, CDCl₃) δ ppm: 0.86 (9H, singlet); 1.21 (3H, doublet, J=6.5 Hz); 2.04 (3H, singlet); 3.08 (1H, doublet of doublets, J=3.0, 2.0 Hz); 3.94–4.35 (1H, multiplet); 6.04 (1H, doublet, J=2.0 Hz).

(2) (3S,4S)-3-[(1R)-1-t-Butyldimethylsilyloxyethyl]-4-[(1R)-1-(phenylthiocarbonyl)ethyl]-2-azetidinone and (3S,4S)-3-[(1R)-1-t-Butyldimethylsilyloxyethyl]-4-[(1RS)-phenylthiocarbonyl)ethyl]-2-azetidinone 4.46 ml of trimethylsilyl trifluoromethanesulfonate were added, under a nitrogen atmosphere, to a solution of 140.0 g of (3R,4R)-4-acetoxy-3-[(1R)-1-t-butyldimethylsilyloxyethyl]-1-trimethylsilyl-2-azetidinone and 93.0 g of S-phenyl trimethylsilylthiopropionate in 920 ml of methylene chloride. The mixture was stirred at room temperature for about 20 hours, then washed with saturated aqueous sodium chloride solution. The solvent was removed, the residue was dissolved in 920 ml of ethanol, 13.1 g of potassium fluoride were added to the solution, and the mixture was stirred at room temperature for 1.5 hours. The reaction mixture was concentrated, and the concentrate was diluted with ethyl acetate and washed with saturated aqueous sodium chloride solution. The solvent was removed and the concentrate was chromatographed through a column packed with 1.3 kg of silica gel. A fraction eluted with a 3/1 mixture of cyclohexane/ethyl acetate was concentrated and the concentrate subjected to fractional crystallization from a 10/1 mixture of cyclohexane/ethyl acetate, giving 41.0 g of (3S,4S)-3-[(1R)-1-t-butyldimethylsilyloxyethyl]-4-[(1R)-1-(phenylthiocarbonyl)ethyl]-2-azetidinone and 82.0 g of (3S,4S)-3-[(1R)-1-t-butyldimethylsilyloxyethyl]-4-[(1RS)-1-(phenylthiocarbonyl)ethyl]-2-azetidinone (R/S ratio nearly 1/1).

(3S,4S)-3-[(1R)-1-t-Butyldimethylsilyloxyethyl]-4-[(1R)-1-(phenylthiocarbonyl)ethyl]-2-azetidinone NMR spectrum (60 MHz, CDCl₃) δ ppm: 0.87 (9H, singlet); 1.20 (3H, doublet, J=7.0 Hz); 1.30 (3H, doublet, J=7.0 Hz); 2.64–3.21 (2H), multiplet); 3.89 (1H, doublet of doublets, J=6.0, 2.0 Hz); 4.02–4.36 (1H, multiplet); 5.90 (1H, broad singlet).

(3S,4S)-3-[(1R)-1-t-Butyldimethylsilyloxyethyl]-4-[(1RS)-1-phenylthiocarbonyl)ethyl]-2-azetidinone NMR spectrum (60 MHz, CDCl₃) δ ppm: 1.20 (1.5H, doublet, J=7.0 Hz); 1.23 (1.5H, doublet, J=6.5 Hz); 1.30 (1.5H, doublet, J=7.0 Hz); 1.33 (1.5H, doublet, J=6.5 Hz); 2.48-3.21 (2H, multiplet); 3.59-4.38 (2H, multiplet); 5.91 (1H, broad singlet).

(3) p-Nitrobenzyl (1RS,5S,6S)-2-phenylthio-6-[(1R)-1-t-butyldimethylsilyloxyethyl]-1-methyl-1-carbapen-2-em-3-carboxylate A solution of 0.71 ml of triethylamine and 1.1 g of p-nitrobenzyloxyoxalyl chloride in 10 ml of methylene chloride was added to a solution of 1 g of (3S,4S)-3-[(1R)-1-t-butyldimethylsilyloxyethyl]-4-[(1RS)-1-(phenylthiocarbonyl)ethyl]-2-azetidinone in 10 ml of methylene chloride, cooled to about −30° C. The mixture was stirred for 35 minutes at −30° C., then 389 μl of isopropanol were added, and the solvent was distilled off. The residue was mixed with 10 ml of anhydrous benzene and the resulting precipitate was filtered off over "Celite" (Trade Mark) filter aid. The filtrate was chromatographed through a short column containing silica gel, eluted with a 2/1 mixture of benzene/ethyl acetate, giving (3S,4S)-3-[(1R)-1-t-butyldimethylsilyloxyethyl]-4-[(1RS)-1-(phenylthiocarbonyl)ethyl]-1-(p-nitrobenzyloxalyl)-2-azetidinone as an oil. This oil was dissolved in 100 ml of toluene and the solution mixed with 2.6 ml of triethyl phosphite. The mixture was heated at 140° C. for about 12 hours under a nitrogen atmosphere. The solvent and excess of triethyl phosphite were distilled off from the reaction mixture, and the product was recovered and purified by chromatography through two Lobar columns (Merck "Li-Chroprep Si60", Size B). 699 mg of p-nitrobenzyl (1RS,5S,6S)-2-phenylthio-6-[(1R)-1-t-butyldimetylsilyloxyethyl]-1-methyl-1-carbapen-2-em-3-carboxylate were obtained from a fraction eluted with a 4/1/1 mixture of cyclohexane/benzene/ethyl acetate.

IR Spectrum $\lambda_{max}^{neat}$ cm$^{-1}$: 1780, 1705, 1605, 1520.

UV Spectrum $\lambda_{max}^{EtOH}$ nm: 263, 323.

NMR spectrum (60 MHz, CDCl$_3$) δ ppm: 0.85 (9H, singlet); 0.92 (3H, doublet, J=7.0 Hz); 1.21 (3H, doublet, J=6.5 Hz); 2.95-4.40 (4H, multiplet); 5.20, 5.48 (2H, AB-quartet, J=14.0 Hz); 7.15-7.60 (5H, multiplet); 7.63, 8.20 (4H, A$_2$B$_2$, J=9.0 Hz).

(4) p-Nitrobenzyl (1RS,5S,6S)-2-phenylthio-6-[(1R)-1-hydroxyethyl]-1-methyl-1-carbapen-2-em-3-carboxylate 300 μl of acetic acid and 2.1 ml of a 1M solution of tetrabutylammonium fluoride in tetrahydrofuran were added to a solution of 298 mg of p-nitrobenzyl (1RS,5S,6S)-2-phenylthio-6-[(1R)-1-t-butyldimethylsilyl-oxyethyl]-1-methyl-1-carbapen-2-em-3-carboxylate in 6.4 ml of tetrahydrofuran, kept at 0° to 5° C. with ice-water cooling. The mixture was kept stirred overnight at room temperature, and then for 4 hours in an oil bath at 30° C. The reaction mixture was then diluted with ethyl acetate and washed successively with saturated aqueous sodium chloride solution, 5% aqueous sodium bicarbonate solution, and again saturated aqueous sodium chloride solution. The solvent was distilled off, and the resulting residue was chromatographed on a column of silica gel using a 3/1 mixture of benzene/ethyl acetate as eluent, giving 57 mg of the title compound as pale yellow crystals.

NMR spectrum (60 MHz, CDCl$_3$) δ ppm: 0.94, 0.96 (3H, doublet, J=7.0 Hz); 1.30 (3H, doublet, J=6.5 Hz); 2.91-4.48 (4H, multiplet); 5.06-5.70 (2H, multiplet); 7.12-7.64 (5H, multiplet); 7.65, 7.22 (4H, A$_2$B$_2$, J=9.0 Hz).

PREPARATION 2 p-Nitrobenzyl(1RS,5S,6S)-2-phenylthio-6-[(1R)-1-hydroxyethyl]-1-methyl-1-carbapen-2-em-3-carboxylate (1) (3S,4S)-3-[(1R)-1-Hydroxyethyl]-4-[(1RS)-1-(phenylthiocarbonyl)ethyl]-2-azetidinone 1.3 ml of boron trifluoride etherate were added to a solution of 1.37 g of (3S,4S)-3-[(1R)-1-t-butyldimethylsilyloxyethyl]-4-[(1RS)-1-(phenylthiocarbonyl)ethyl]-2-azetidinone in 33 ml of acetonitrile, cooled in ice-water, and the mixture was stirred for 15 minutes at 0° to 5° C. 2.94 g of sodium bicarbonate were added to the reaction mixture, then a saturated aqueous sodium chloride solution was added, and the mixture was extracted with ethyl acetate. The organic layer was washed with saturated aqueous sodium chloride solution and dried over anhydrous magnesium sulfate. The solvent was stripped off, giving 0.95 g of (3S,4S)-3-[(1R)-1-hydroxyethyl]-4-[(1RS)-1-(phenylthiocarbonyl)ethyl]-2-azetidinone, which was used in the following reaction.

(2) (3S,4S)-3-[(1R)-1-Trimethylsilyloxyethyl]-4-[(1RS)-1-(phenylthiocarbonyl)ethyl]-2-azetidinone 1.33 ml of trimethylsilyl chloride and 1.46 ml of triethylamine were added to a solution of 0.95 g of (3S,4S)-3-[(1R)-1-hydroxyethyl-4-[(1RS)-1-(phenylthiocarbonyl)ethyl]-2-azetidinone in 30 ml of methylene chloride kept at 0° to 5° C. with ice-water cooling, and the mixture was stirred at the same temperature for about 30 minutes. 10 g of silica gel were then added, and the mixture was stirred for about 5 hours. The reaction mixture was chromatographed on a column of silica gel, and a fraction eluted with a 4/1 mixture of cyclohexane/ethyl acetate was worked up to give 0.914 g of (3S,4S)-3-[(1R)-1-trimethylsilyloxyethyl]-4-[(1RS)-1-(phenylthiocarbonyl)ethyl]-2-azetidinone as an oil.

NMR spectrum (60 MHz, CDCl$_3$) δ ppm: 0.11 (9H, singlet); 1.14-1.39 (6H, multiplet); 2.64-4.32 (4H, multiplet); 5.97 (1H, broad singlet); 7.34 (5H, singlet).

(3) p-Nitrobenzyl(1RS,5S,6S)-2-phenylthio-6-[(1R)-1-hydroxyethyl]-1-methyl-1-carbapen-2-em-3-carboxylate A solution of 0.71 ml of triethylamine and 1.1 g of p-nitrobenzyloxyoxalyl chloride in 10 ml of methylene chloride was added to a solution of 0.9 g of (3S,4S)-3-[(1R)-1-trimethylsilyloxyethyl]-4-[(1RS)-1-(phenylthiocarbonyl)ethyl]-2-azetidinone in 10 ml of methylene chloride, cooled to about −30° C., and the mixture was stirred for 35 minutes at the same temperature. The reaction mixture was worked up and purified in the same manner as in Preparation 1(3), giving (3S,4S)-3-[(1R)-1-trimethylsilyloxyethyl]-4-[(1RS)-1-(phenylthiocarbonyl)ethyl]-1-(p-nitrobenzyloxyoxalyl)-2-azetidinone as an oil.

This oil was dissolved in 100 ml of toluene and the solution mixed with 2.6 ml of triethyl phosphite. The resulting mixture was heated at 140° C. for about 12 hours under a nitrogen atmosphere. The solvent and excess triethyl phosphite were distilled off under reduced pressure. The residue was dissolved in 14 ml of a 4/1 mixture of tetrahydrofuran and water, mixed with 70 mg of pyridinium p-toluenesulfonate, and allowed to stand for one hour at room temperature. A saturated aqueous solution of sodium chloride was added, and the mixture was extracted with ethyl acetate. The organic layer was dried over anhydrous magnesium sulfate and the solvent was distilled off. The residue was chromatographed over silica gel, in the same manner as in Preparation 1(4), giving 382 mg of the title compound with the same NMR spectrum and thin layer chromatography results as the product of Preparation 1(4).

PREPARATION 3 p-Nitrobenzyl(1RS,5S,6S)-2-phenylsulfinyl-6-[(1R)-1-hydroxyethyl]-1-methyl-1-carbapen-2-em-3-carboxylate 19 ml of saturated aqueous sodium bicarbonate solution and a solution of 350 mg of 3-chloroperbenzoic acid in 10 ml of methylene chloride were added to a solution of 360 mg of p-nitrobenzyl(1RS,5S,6S)-2-phenylthio-6-[(1R)-1-hydroxyethyl]-1-methyl-1-carbapen-2-em-3-carboxylate in 19 ml of methylene chloride, kept at 0° to 5° C. with ice-water cooling, and the mixture was stirred for 35 minutes at the same temperature. The reaction mixture was then diluted with methylene chloride and washed with saturated aqueous sodium chloride solution. The organic layer was dried over anhydrous magnesium sulfate and the solvent was distilled off. The residue was purified by chromatography on a column of silica gel, using a ⅓ mixture of benzene and ethyl acetate as eluent, giving 200 mg of the title compound.

NMR spectrum (60 MHz, CDCl$_3$) δ ppm: 0.80 (3H, doublet, J=7.0 Hz); 1.32 (3H, doublet, J=6.5 Hz); 2.92–4.60 (4H, multiplet); 5.18–5.70 (2H, multiplet); 7.24–7.80 (5H, multiplet); 7.63, 8.21 (4H, A$_2$B$_2$, J=9.0 Hz).

PREPARATION 4

(3R)-3-Carbamoyloxypyrrolidine hydrochloride (1) (3R)-1-(t-Butoxycarbonyl)-3-carbamoyloxypyrrolidine A solution of 4.52 g of trichloroacetyl isocyanate in 8 ml of methylene chloride was added to an ice-cooled solution of 3.75 g of (3R)-1-(t-butoxycarbonyl)-3-hydroxypyrrolidine in 40 ml of methylene chloride, and the mixture was stirred for 30 minutes with ice-cooling. After completion of the reaction, the solvent was stripped off from the reaction mixture and the residue was dissolved in 100 ml of methanol. The solution was stirred with 35 g of silica gel for 5 hours at 30° C., and then filtered. The filtrate was concentrated, giving 3.05 g of (3R)-1-(t-butoxycarbonyl)-3-carbamoyloxypyrrolidine.

NMR spectrum (60 MHz, CDCl$_3$) δ ppm: 1.48 (9H, singlet); 1.78–2.30 (2H, multiplet); 3.15–3.76 (4H, multiplet); 4.82 (2H, broad singlet); 5.15 (1H, quintet, J=3.5 Hz).

(2) (3R)-3-Carbamoyloxypyrrolidine hydrochloride 15 ml of a 4M hydrogen chloride solution in ethyl acetate was added to a suspension of 3.00 g of (3R)-1-(t-butoxycarbonyl)-3-carbamoyloxypyrrolidine in 30 ml of methylene chloride, and the mixture was stirred for 30 minutes at 30° C. After completion of the reaction, the precipitated crystals were collected by filtration and washed with ether, giving 1.78 g of the title compound.

NMR spectrum (60 MHz, D$_2$O) δ ppm: 2.00–2.46 (2H, multiplet); 3.26–3.65 (4H, multiplet); 5.28 (1H, quintet, J=3.5 Hz).

PREPARATION 5

4-Hydroxyiminopiperidine hydrochloride 5.4 ml of 28% aqueous ammonia solution were added to a mixture of 3.0 g of 4-piperidone hydrochloride monohydrate and 1.63 g of hydroxylamine hydrochloride, and the resulting mixture was stirred for 2 hours at 80° to 90° C. After completion of the reaction, the solvent was distilled off and the crystalline residue was recrystallized from methanol, giving 1.8 g of the title compound.

Melting point: <220° C.

NMR spectrum (60 MHz, D$_2$O) δ ppm: 2.42–2.98 (4H, multiplet); 3.17–3.54 (4H, multiplet).

PREPARATION 6

4-Methoxyiminopiperidine 53 ml of anhydrous pyridine were added to a mixture of 3.34 g of 4-piperidone hydrochloride monohydrate and 2.0 g of o-methylhydroxylamine hydrochloride, and the mixture was kept stirred overnight at room temperature. After completion of the reaction, the solvent was distilled off, and the crystalline residue was washed with ethyl acetate and collected by filtration. The crystals were washed with saturated aqueous sodium bicarbonate solution until basic and then extracted with chloroform. The chloroform layer was dried over anhydrous magnesium sulfate and the solvent was stripped off, giving 2.5 g of the title compound.

NMR spectrum (60 MHz, CDCl$_3$) δ ppm: 1.72 (1H, singlet); 2.11–2.63 (4H, multiplet); 2.75–3.06 (4H, multiplet); 3.77 (3H, singlet).

PREPARATON 7

3-Methoxyiminopyrrolidine hydrochloride (1) 1-(t-Butoxycarbonyl)-3-pyrrolidone

A solution of 3.4 ml of dimethylsulfoxide in 10 ml of methylene chloride was added to a solution of 2.0 ml oxalyl chloride in 50 ml of methylene chloride, maintained at −50° to −60° C., and immediately afterwards a solution of 3.74 g of (3R)-1-(t-butoxycarbonyl)-3-hydroxypyrrolidine in 20 ml of methylene chloride was added to the mixture over a period of about 2 minutes. The reaction mixture was kept stirred for 15 minutes at −50° to −60° C., and then 14 ml of triethylamine were added to it. The mixture was stirred at the same temperature for a further 5 minutes, and the stirring was then continued while allowing its temperature to rise to ambient. The reaction mixture was mixed with 100 ml of water and extracted with methylene chloride. The organic extract was washed with saturated aqueous sodium chloride solution and dried over anhydrous magnesium sulfate. The solvent was distilled off and the residue was chromatographed on a silica gel column, eluted with a 2/1 mixture of benzene and ethyl acetate, giving 3.61 g of 1-(t-butoxycarbonyl)-3-pyrrolidone as an oil.

NMR spectrum (60 MHz, CDCl$_3$) δ ppm: 1.48 (9H, singlet); 2.55 (2H, triplet, J=7.0 Hz); 3.72 (1H, singlet); 3.74 (2H, triplet, J=7.0 Hz).

(2) 1-(t-Butoxycarbonyl)-3-methoxyiminopyrrolidine 27 ml of anhydrous pyridine were added to a mixture of 2.0 g of 1-(t-butoxycarbonyl)-3-pyrrolidone and 992 mg of o-methylhydroxylamine hydrochloride, and the mixture was kept stirred overnight at room temperature. After completion of the reaction, the solvent was distilled off and saturated aqueous sodium bicarbonate solution was added to the residue until it was basic. The mixture was extracted with chloroform, and the extract was dried over anhydrous magnesium sulfate and concentrated. The residue was chromatographed over silica gel, using a 3/1 mixture of benzene and ethyl acetate as eluent, giving 2.3 g of 1-(t-butoxycarbonyl)-3-methoxyiminopyrrolidine as a mixture of syn- and anti-isomers.

IR Spectrum $\nu_{max}^{neat}$ cm$^{-1}$: 1700.

NMR spectrum (60 MHz, CDCl$_3$) δppm: 1.47 (9H, singlet); 2.64 (2H, triplet, J=7.0 Hz); 3.53 (2H, triplet, J=7.0 Hz); 3.82 (3H, singlet); 4.00 (2H, singlet).

(3) 3-Methoxyiminopyrrolidine hydrochloride 7 ml of a 3M hydrogen chloride solution in ethyl acetate was added to 2.3 g of ice-cooled 1-(t-butoxycarbonyl)-3-methoxyiminopyrrolidine, and the mixture was stirred at about 40° C. for one hour. After completion of the reaction, the solvent was stripped off from the reaction mixture and ether was added to the residue. The crystals which formed were collected by filtration and washed with ether, giving 1.5 g of the title compound.

NMR spectrum (60 MHz, D$_2$O) δppm: 2.84 (2H, triplet, J=7.0 Hz); 2.59 (2H, triplet, J=7.0 Hz); 3.87 (3H, singlet); 4.05 (1H, broad singlet).

PREPARATION 8

3-Hydroxyiminopyrrolidine hydrochloride (1) 1-(t-Butoxycarbonyl)-3-hydroxyiminopyrrolidine 1.87 g of hydroxylamine hydrochloride and 3.3 ml of pyridine were added to a solution of 2.0 g of 1-(t-butoxycarbonyl)-3-pyrrolidone in 9 ml of ethanol, and the mixture was refluxed for 2 hours. The solvent was then distilled off from the reaction mixture, saturated aqueous sodium bicarbonate solution was added to the residue, and it was extracted with chloroform. The chloroform extract was dried over anhydrous magnesium sulfate and the solvent was distilled off. The residue was chromatographed on a silica gel column, using a 2/1 mixture of benzene and ethyl acetate as eluent, giving 1.482 g of 1-(t-butoxycarbonyl)-3-hydroxyiminopyrrolidine as a mixture of syn- and anti-isomers.

NMR Spectrum (60 MHz, DMSO-d$_6$): 1.42 (9H, singlet); 2.28–3.95 (6H, multiplet); 3.28 (1H, singlet).

(2) 3-Hydroxyiminopyrrolidine hydrochloride 5 ml of a 3M hydrogen chloride solution in ethyl acetate was added to 1.4 g of ice-cooled 1-(t-butoxycarbonyl)-3-hydroxyiminopyrrolidine and the mixture was stirred at about 40° C. for one hour. After completion of the reaction, the solvent was distilled off and ether was added to the residue. The crystals which separated out were collected by filtration and washed with ether, giving 950 mg of the title compound.

NMR spectrum (60 MHz, D$_2$O) δppm: 2.36–4.02 (6H, multiplet).

PREPARATIONS 9 & 10

The following intermediates were prepared by following the procedure of Preparation 4 but using, respectively, 1-(t-butoxycarbonyl)-4-hydroxypiperidine or 1-(t-butoxycarbonyl)-(3RS)-3-hydroxypiperidine as the starting material.

PREPARATION 9

(1) 1-(t-Butoxycarbonyl)-4-carbamoyloxypiperidine

NMR Spectrum (60 MHz, CDCl$_3$) δppm: 1.16–2.10 (4H, multiplet); 1.47 (9H, singlet); 4.41–5.28 (3H, multiplet).

(2) 4-Carbamoyloxypiperidine hydrochloride

NMR Spectrum (60 MHz, D$_2$O) δppm: 1.53–2.22 (4H, multiplet); 2.91–3.56 (4H, multiplet); 4.61–5.03 (1H, multiplet).

PREPARATION 10

(1) 1-(t-Butoxycarbonyl)-(3RS)-3-carbamoyloxypiperidine

NMR Spectrum (60 MHz, CDCl$_3$) δppm: 1.06–2.13 (4H, multiplet); 2.87–3.73 (4H, multiplet); 4.38–4.94 (1H, multiplet); 5.13 (2H, broad singlet).

(2) (3RS)-3-Carbamoyloxypiperidine hydrochloride

NMR Spectrum (60 MHz, D$_2$O) δppm: 1.41–2.25 (4H, multiplet); 2.76–3.63 (4H, multiplet); 4.65–5.12 (1H, singlet).

PREPARATION 11

(2S,4R)-2-Carbamoyl-4-hydroxypyrrolidine hydrochloride (1) (2S,4R)-1-(t-Butoxycarbonyl)-2-carbamoyl-4-hydroxypyrrolidine A solution of 4.98 ml of ethyl chloroformate in 50 ml of anhydrous tetrahydrofuran was added, under cooling at −+° C., to a solution of 11.0 g of 1-(t-butoxycarbonyl)-(2S,4R)-4-hydroxy-2-pyrrolidinecarboxylic acid and 7.25 ml of triethylamine in 160 ml of anhydrous tetrahydrofuran, and the mixture was stirred at the same temperature for one hour. 50 ml of concentrated aqueous ammonia were then added, at the same temperature, and the mixture was allowed to stand while its temperature rose to ambient. The reaction mixture was stirred for one hour, and then concentrated by evaporation under reduced pressure. A saturated aqueous solution of sodium chloride was added to the concentrate, which was then extracted three times with ethyl acetate. The extract was dried over anhydrous magnesium sulfate and then concentrated under reduced pressure, to give 7.70 g of (2S,4R)-1-(t-butoxycarbonyl-2-carbamoyl-4-hydroxypyrrolidine.

NMR Spectrum (60 MHz, DMSO-d$_6$) δppm: 1.38 (9H, singlet); 1.65–2.24 (2H, multiplet); 3.00–3.66 (2H, multiplet); 3.76–4.49 (3H, multiplet); 6.78 (1H, broad singlet); 7.23 (1H, broad singlet).

(2) (2S,4R)-2-Carbamoyl-4-hydroxypyrrolidine hydrochloride 4.50 g of the product obtained in step (1) above were suspended in 45 ml of ethyl acetate and then 14.9 ml of 4.84M hydrogen chloride in ethyl acetate were added under ice-cooling. The mixture was stirred at 25°–30° C. for 30 minutes, after which the reaction mixture was worked up in the same manner as in Preparation 4(2) to give 3.21 g of the title compound.

NMR Spectrum (60 MHz, DMSO-d$_6$) δppm: 1.57–2.60 (2H, multiplet); 2.75–3.70 (2H, multiplet); 3.91–4.70 (2H, multiplet); 4.84 (1H, broad singlet); 7.61 (1H, broad singlet); 8.16 (1H, broad singlet).

PREPARATION 12

The following intermediates were prepared by the procedure of Preparation 4, but using (2S,4R)-1-(t-butoxycarbonyl)-2-carbamoyl-4-hydroxypyrrolidine as the startig material.

(1) (2S,4R)-1-(t-Butoxycarbonyl)-2-carbamoyl-4-carbamoyloxypyrrolidine

NMR Spectrum (60 MHz, DMSO-d$_6$) δppm: 1.43 (9H, singlet); 1.91–2.50 (2H, multiplet); 3.12–3.70 (2H, multiplet); 3.96–4.43 (1H, multiplet); 4.80–5.29 (1H, multiplet); 6.34 (1H, broad singlet); 6.80 (1H, broad singlet); 7.31 (1H, broad singlet); 8.10 (1H, broad singlet).

(2) (2S,4R)-2-Carbamoyl-4-carbamoyloxypyrrolidine hydrochloride

NMR Spectrum (60 MHz, DMSO-d$_6$) δppm: 1.73–2.82 (2H, multiplet); 2.86–3.98 (2H, multiplet); 4.00–4.58 (1H, multiplet); 4.82–5.31 (1H, multiplet); 6.61 (2H, broad singlet); 7.67 (1H, broad singlet); 8.22 (1H, broad singlet).

PREPARATION 13

The following intermediates were prepared by the procedure of Preparation 11, but using 1-(t-butoxycarbonyl)-L-proline as the starting material.

(1) (2S)-1-(t-Butoxycarbonyl)-2-carbamoylpyrrolidine

NMR Spectrum (60 MHz, CDCl$_3$) δppm: 1.47 (9H, singlet); 1.65–2.49 (4H, multiplet); 3.17–3.69 (2H, multiplet); 4.03–4.48 (1 H, multiplet); 5.40–6.80 (2H, multiplet).

(2) (2-Carbamoylpyrrolidine hydrochloride

NMR Spectrum (60 MHz, D$_2$O) δppm: 1.83–2.80 (4H, multiplet); 3.22–3.68 (2H, multiplet); 4.19–4.62 (1H, multiplet).

PREPARATION 14

1-Methyl-2-oxopiperazine hydrochloride (1) 1-Methyl-2-oxo-4-t-butoxycarbonylpiperazine 8 g of 4-t-butoxycarbonyl-2-oxopiperazine (previously prepared from 2-oxopiperazine and di-t-butyl dicarbonate) were dissolved in 80 ml of dimethylformamide. 1.92 g of sodium hydride (55%, in paraffin) were added to this solution, and the mixture was stirred at room temperature for one hour. A solution of 6.8 g of methyl iodide in 20 ml of dimethylformamide was then added, and the resulting mixture was stirred at room temperature for 3 hours. The reaction mixture was then poured into a saturated aqueous solution of sodium chloride and extracted with ethyl acetate. The extract was washed with water and dried over anhydrous magnesium sulfate. The solvent was distilled off and the residue was purified by column chromatography through silica gel, eluted with ethyl acetate, to give 3.0 g of 1-methyl-2-oxo-4-t-butoxycarbonylpiperazine in the form of colorless oil.

NMR Spectrum (60 MHz, CDCl$_3$) δ ppm: 1.46 (9H, singlet); 3.00 (3H, singlet); 3.20–3.80 (4H, multiplet); 4.05 (2H, singlet).

(2) 1-Methyl-2-oxopiperazine hydrochloride 14 ml of 3M hydrogen chloride in ethyl acetate were added to 3.0 g of the product obtained in step (1) above, and the mixture was stirred at 35° C. for one hour. Diethyl ether was added to the reaction mixture, and the crystals which precipitated out were collected by filtration, washed with diethyl ether and dried, to give 2.1 g of the title compound.

NMR Spectrum (60 MHz, D$_2$O) δ ppm: 2.91 (3H, singlet); 3.53 (4H, singlet); 3.82 (2H, singlet).

We claim:

1. A compound having the formula:

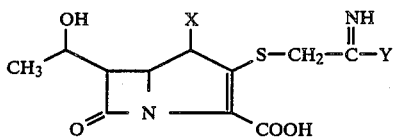

wherein

X represents a hydrogen atom or a methyl group; and
Y represents a group of the formula:

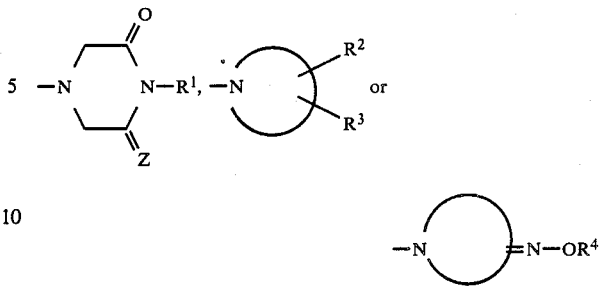

in which:

Z represents an oxygen atom or two hydrogen atoms;
R$^1$ represents a hydrogen atom, a C$_{1-4}$ alkyl group, a C$_{1-4}$ alkanoyl group, or a C$_{1-4}$ alkanesulfonyl group;
R$^2$ represents a hydrogen atom or a hydroxy group, and R$^3$ represents a carbamoyl group; or
R$^2$ represents a carbamoyloxy group, and R$^3$ represents a hydrogen atom or a carbamoyl group;
R$^4$ represents a hydrogen atom or a C$_{1-4}$ alkyl group; and

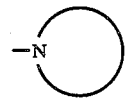

represents a 4–6 membered saturated heterocyclic group in which the indicated nitrogen atom is the only hetero-atom;

or a pharmaceutically acceptable salt or ester thereof.

2. The compound as claimed in claim 1, wherein R$^1$ is selected from the group consisting of a hydrogen atom, a methyl group, an acetyl group and a methanesulphonyl group.

3. The compound as claimed in claim 1, wherein Y is selected from the group consisting of a 3-oxopiperazin-1-yl group, a 4-methyl-3-oxopiperazin-1-yl group, a carbamoyloxypyrrolidin-1-yl group, a hydroxyiminopiperidin-1-yl group and a methoxyiminopiperidin-1-yl group.

4. The compound as claimed in claim 1, wherein R$^1$ is selected from the group consisting of a hydrogen atom and a methyl group, and Y is selected from the group consisting of a 3-oxopiperazin-1-yl group and a 4-methyl-3-oxopiperazin-1-yl group.

5. The compound of claim 1 which is (5R,6S)-2-[2-(3-oxopiperazin-1-yl)-2-iminoethylthio]-6-[(1R)-1-hydroxyethyl]-1-carbapen-2-em-3-carboxylic acid.

6. The compound of claim 1 which is (1R,5S,6S)-2-[2-(3-oxopiperazin-1-yl)-2-iminoethylthio]-6-[(1R)-1-hydroxyethyl]-1-methyl-1-carbapen-2-em-3-carboxylic acid.

7. The compound of claim 1 which is (5R,6S)-2-[2-(4-methyl-3-oxopiperazin-1-yl)-2-iminoethylthio]-6-[(1R)-1-hydroxyethyl]-1-carbapen-2-em-3-carboxylic acid.

8. The compound of claim 1 which is (1R,5S,6S)-2-[2-(4-methyl-3-oxopiperazin-1-yl)-2-iminoethylthio]-6-[(1R)-1-hydroxyethyl]-1-methyl-1-carbapen-2-em-3-carboxylic acid.

9. The compound of claim 1 which is (5R,6S)-2-[2-(3,5-dioxopiperazin-1yl)-2-iminoethylthio]-6-[(1R)-1-hydroxyethyl]-1-carbapen-2-em-3-carboxylic acid.

10. The compound of claim 1 which is (1R,5S,6S)-2-[2-(3,5-dioxopiperazin-1-yl)-2-iminoethylthio]-6-[(1R)-1-hydroxyethyl]-1-methyl-1-carbapen-2-em-3-carboxylic acid.

11. The compound of claim 1 which is (5R,6S)-2-{2-[(3R)-3-carbamoyloxypyrrolidin-1-yl]-2-iminoethylthio}-6-[(1R)-1-hydroxyethyl]-1-carbapen-2-em-3-carboxylic acid.

12. The compound of claim 1 which is (1R,5S,6S)-2-{2-[(3R)-3-carbamoyloxypyrrolidin-1-yl]-2-iminoethylthio}-6-[(1R)-1-hydroxyethyl]-1-methyl-1-carbapen-2-em-3-carboxylic acid.

13. The compound of claim 1 which is (5R,6S)-2-[2-(4-hydroxyiminopiperidin-1-yl)-2-iminoethylthio]-6-[(1R)-1-hydroxyethyl]-1-carbapen-2-em-3-carboxylic acid.

14. The compound of claim 1 which is (1R,5S,6S)-2-[2-(4-hydroxyiminopiperidin-1-yl)-2-iminoethylthio]-6-[(1R)-1-hydroxyethyl]-1-methyl-1-carbapen-2-em-3-carboxylic acid.

15. A pharmaceutical composition comprising an effective amount of an antibacterial agent in admixture with a pharmaceutically acceptable carrier or diluent, wherein the antibacterial agent is a compound of formula

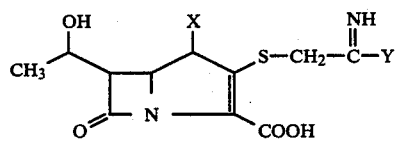

wherein:
X represents a hydrogen atom or a methyl group; and
Y represents a group of the formula:

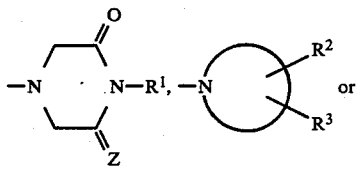

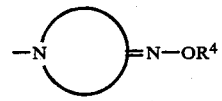

in which:
Z represents an oxygen atom or two hydrogen atoms;
$R^1$ represents a hydrogen atom, a $C_{1-4}$ alkyl group, a $C_{1-4}$ alkanoyl group, or a $C_{1-4}$ alkanesulfonyl group;
$R^2$ represents a hydrogen atom or a hydroxy group, and $R^3$ represents a carbamoyl group; or
$R^2$ represents a carbamoyloxy group, and $R^3$ represents a hydrogen atom or a carbamoyl group;

$R^4$ represents a hydrogen atom or a $C_{1-4}$ alkyl group; and

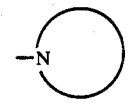

represents a 4–6 membered saturated heterocyclic group in which the indicated nitrogen atom is the only hetero-atom;
or a pharmaceutically acceptable salt or ester thereof.

16. The composition as claimed in claim 15, wherein $R^1$ is selected from the group consisting of a hydrogen atom, a methyl group, an acetyl group and a methanesulphonyl group.

17. The composition as claimed in claim 15, wherein Y is selected from the group consisting of a 3-oxopiperazin-1-yl group, a 4-methyl-3-oxopiperazin-1-yl group, a carbamoyloxypyrrolidin-1-yl group, a hydroxyiminopiperidin-1-yl group and a methoxyiminopiperidin-1-yl group.

18. The composition as claimed in claim 15, wherein $R^1$ is selected from the group consisting of a hydrogen atom and a methyl group, and Y is selected from the group consisting of a 3-oxopiperazin-1-yl group and a 4-methyl-3-oxopiperazin-1-yl group.

19. The composition as claimed in claim 15, wherein said antibacterial agent is selected from the group consisting of:

(5R,6S)-2-[2-(3-oxopiperazin-1-yl)-2-iminoethylthio]-6-[(1R)-1-hydroxyethyl]-1-carbpen-2-em-3-carboxylic acid (1R,5S,6S)-2-[2-(3-oxopiperazin-1-yl)-2-iminoethylthio]-6-[(1R)-1-hydroxyethyl]-1-methyl-1-carbapen-2-em-3-carboxylic acid (5R,6S)-2-[2-(4-methyl-3-oxopiperazin-1-yl)-2-iminoethylthio]-6-[(1R)-1-hydroxyethyl]-1-carbapen-2-em-3-carboxylic acid (1R,5S,6S)-2-[2-(4-methyl-3-oxopiperazin-1-yl)-2-iminoethylthio]-6-[(1R)-1-hydroxyethyl]-1-methyl-1-carbapen-2-em-3-carboxylic acid (5R,6S)-2-[2-(3,5-dioxopiperazin-1-yl)-2-iminoethylthio]-6-[(1R)-1-hydroxyethyl]-1-carbapen-2-em-3-carboxylic acid (1R,5S,6S)-2-[2-(3,5-dioxopiperazin-1-yl)-2-iminoethylthio]-6-[(1R)-1-hydroxyethyl]-1-methyl-1-carbapen-2-em-3-carboxylic acid (5R,6S)-2-{2-[(3R)-3-carbamoyloxypyrrolidin-1-yl]-2-iminoethylthio}-6-[(1R)-1-hydroxyethyl]-1-carbapen-2-em-3-carboxylic acid (1R,5S,6S)-2-{2-[(3R)-3-carbamoyloxypyrrolidin-1-yl]-2-iminoethylthio}-6-[(1R)-1-hydroxyethyl]-1-methyl-1-carbapen-2-em-3-carboxylic acid (5R,6S)-2-[2-(4-hydroxyiminopiperidin-1-yl)-2-iminoethylthio]-6-[(1R)-1-hydroxyethyl]-1-carbapen-2-em-3-carboxylic acid and (1R,5S,6S)-2-[2-(4-hydroxyiminopiperidin-1-yl)-2-iminoethylthio]-6-[(1R)-1-hydroxyethyl]-1-methyl-1-carbapen-2-em-3-carboxylic acid.

* * * * *